United States Patent
Parakininkas et al.

(10) Patent No.: US 11,609,042 B2
(45) Date of Patent: Mar. 21, 2023

(54) MULTI-PART LYOPHILIZATION CONTAINER AND METHOD OF USE

(71) Applicant: Terumo BCT Biotechnologies, LLC, Lakewood, CO (US)

(72) Inventors: Kestas P. Parakininkas, Englewood, CO (US); Eric T. Hansen, Thornton, CO (US); Kirk L. Weimer, Green Valley, AZ (US); Nathaniel T. Johnson, Highlands Ranch, CO (US); Dennis J. Hlavinka, Arvada, CO (US)

(73) Assignee: Terumo BCT Biotechnologies, LLC, Lakewood, CO (US)

( * ) Notice: Subject to any disclaimer, the term of this patent is extended or adjusted under 35 U.S.C. 154(b) by 0 days.

(21) Appl. No.: 16/815,843

(22) Filed: Mar. 11, 2020

(65) Prior Publication Data
US 2020/0288703 A1 Sep. 17, 2020

Related U.S. Application Data

(60) Provisional application No. 62/818,214, filed on Mar. 14, 2019, provisional application No. 62/952,752, (Continued)

(51) Int. Cl.
*F26B 5/06* (2006.01)
*A61M 1/02* (2006.01)
(Continued)

(52) U.S. Cl.
CPC .............. *F26B 5/06* (2013.01); *A01N 1/0263* (2013.01); *A01N 1/0284* (2013.01);
(Continued)

(58) Field of Classification Search
CPC .......... F26B 5/06; F26B 25/06; B65D 51/241; A61M 1/0277; A61M 2205/584;
(Continued)

(56) References Cited

U.S. PATENT DOCUMENTS

| 136,036 A | 2/1873 | Craven |
| 1,441,570 A | 1/1923 | Fitzgerald |

(Continued)

FOREIGN PATENT DOCUMENTS

| AU | 517248 B2 | 7/1981 |
| AU | 590193 B2 | 11/1989 |

(Continued)

OTHER PUBLICATIONS

US 8,359,766 B2, 01/2013, Hubbard, Jr. et al. (withdrawn)
(Continued)

*Primary Examiner* — Stephen M Gravini
(74) *Attorney, Agent, or Firm* — Harness, Dickey & Pierce, P.L.C.

(57) ABSTRACT

Provided is a multi-part lyophilization container for lyophilizing a fluid, storing the lyophilizate, reconstituting the lyophilizate, and infusing the reconstituted lyophilizate into a patient, including a method of using same. The container includes a front surface, a back surface, a non-breathable section including a port region, a breathable section including a breathable membrane, and a peelable region including a peelable seal encompassing a boundary between the non-breathable section and the breathable section. The method includes inputting a fluid into a non-breathable section of the container, freezing the fluid, applying, in a lyophilization chamber, vacuum pressure, opening the peelable seal using a pressure differential, applying heat energy, sublimating the fluid and creating a temporary occlusion in a peelable region of the container.

22 Claims, 8 Drawing Sheets

Related U.S. Application Data filed on Dec. 23, 2019, provisional application No. 62/971,072, filed on Feb. 6, 2020.

(51) Int. Cl.
| | |
|---|---|
| *A01N 1/02* | (2006.01) |
| *A61J 1/10* | (2006.01) |
| *A61J 1/14* | (2006.01) |
| *B65D 51/24* | (2006.01) |
| *F26B 25/06* | (2006.01) |
| *F26B 21/14* | (2006.01) |
| *F26B 25/18* | (2006.01) |

(52) U.S. Cl.
CPC .............. *A01N 1/0289* (2013.01); *A61J 1/10* (2013.01); *A61M 1/0277* (2014.02); *F26B 21/14* (2013.01); *A01N 1/0252* (2013.01); *A61J 1/1468* (2015.05); *A61M 2202/0415* (2013.01); *A61M 2205/3389* (2013.01); *A61M 2205/584* (2013.01); *B65D 51/241* (2013.01); *F26B 25/063* (2013.01); *F26B 25/18* (2013.01)

(58) Field of Classification Search
CPC .. A61M 2205/3389; A61M 2202/0415; A01N 1/0263; A01N 1/0284; A01N 1/0289
USPC ......................................................... 34/296
See application file for complete search history.

(56) References Cited

U.S. PATENT DOCUMENTS

| | | | |
|---|---|---|---|
| 1,504,225 A | 8/1924 | Fitzgerald |
| 1,956,784 A | 5/1934 | Allen |
| 2,659,986 A | 11/1953 | Hink, Jr. |
| 2,704,075 A | 3/1955 | Cherkin |
| 2,767,117 A | 10/1956 | Crawley |
| 2,893,843 A | 7/1959 | Adams, Jr. |
| 2,912,359 A | 11/1959 | Anigstein et al. |
| 3,008,879 A | 11/1961 | Harvill |
| 3,024,167 A | 3/1962 | Damaskus |
| 3,057,781 A | 10/1962 | Moore et al. |
| 3,123,443 A | 3/1964 | Smeby |
| 3,187,750 A | 6/1965 | Tenczar |
| 3,223,593 A | 12/1965 | Aldrich et al. |
| 3,228,841 A | 1/1966 | Cohen et al. |
| 3,229,813 A | 1/1966 | Crowe, Jr. et al. |
| 3,236,732 A | 2/1966 | Arquilla |
| 3,247,957 A | 4/1966 | Kemble |
| 3,260,648 A | 7/1966 | Fox |
| 3,294,523 A | 12/1966 | Morningstar |
| 3,322,634 A | 5/1967 | Fulthorpe |
| 3,375,824 A | 4/1968 | Krakauer et al. |
| 3,395,210 A | 7/1968 | Lenahan et al. |
| 3,423,290 A | 1/1969 | Chappelle |
| 3,453,180 A | 7/1969 | Fraser, Jr. et al. |
| 3,466,249 A | 9/1969 | Anderson |
| 3,468,471 A | 9/1969 | Linder |
| 3,490,437 A | 1/1970 | Bakondy et al. |
| 3,519,572 A | 7/1970 | Kita |
| 3,533,934 A | 10/1970 | Armanini |
| 3,537,189 A | 11/1970 | Bender et al. |
| 3,548,051 A | 12/1970 | Hamilton |
| 3,556,760 A | 1/1971 | Bender et al. |
| 3,565,987 A | 2/1971 | Schuurs |
| 3,571,940 A | 3/1971 | Bender |
| 3,573,063 A | 3/1971 | Williams |
| 3,574,950 A | 4/1971 | Dantoni |
| 3,607,858 A | 9/1971 | Querry et al. |
| 3,627,878 A | 12/1971 | Linsner |
| 3,629,142 A | 12/1971 | Marbach |
| 3,674,860 A | 7/1972 | Welter et al. |
| 3,714,345 A | 1/1973 | Hirata |
| 3,717,708 A | 2/1973 | Wada et al. |
| 3,730,843 A | 5/1973 | McKie, Jr. |
| 3,799,740 A | 3/1974 | Mincey |
| 3,803,299 A | 4/1974 | Nouel |
| 3,831,293 A | 8/1974 | Ingram et al. |
| 3,859,047 A | 1/1975 | Klein |
| 3,922,145 A | 11/1975 | Turner et al. |
| 3,932,943 A | 1/1976 | Briggs et al. |
| 3,944,665 A | 3/1976 | Galoian et al. |
| 3,945,523 A | 3/1976 | Wertlake et al. |
| 3,964,865 A | 6/1976 | Das |
| 3,973,002 A | 8/1976 | Hagan et al. |
| 3,987,159 A | 10/1976 | Spona et al. |
| 3,993,585 A | 11/1976 | Pinto et al. |
| 4,001,944 A | 1/1977 | Williams |
| 4,002,739 A | 1/1977 | Turner et al. |
| 4,035,924 A | 7/1977 | Faure |
| 4,045,176 A | 8/1977 | Proksch et al. |
| 4,049,673 A | 9/1977 | Scheinberg |
| 4,056,484 A | 11/1977 | Heimburger et al. |
| 4,059,491 A | 11/1977 | Iwasa et al. |
| 4,080,265 A | 3/1978 | Antonik |
| 4,089,944 A | 5/1978 | Thomas |
| 4,109,396 A | 8/1978 | Fraser |
| 4,127,502 A | 11/1978 | Li Mutti et al. |
| 4,134,943 A | 1/1979 | Knitsch et al. |
| 4,141,856 A | 2/1979 | Dorwart, Jr. et al. |
| 4,141,887 A | 2/1979 | Seufert |
| 4,155,186 A | 5/1979 | Robinson |
| 4,157,383 A | 6/1979 | Sedlacek et al. |
| 4,188,318 A | 2/1980 | Shanbrom |
| 4,189,400 A | 2/1980 | Proksch et al. |
| 4,202,665 A | 5/1980 | Wenz et al. |
| 4,218,321 A | 8/1980 | Sasaki et al. |
| 4,249,826 A | 2/1981 | Studievic et al. |
| 4,284,725 A | 8/1981 | Fennel, III et al. |
| 4,287,087 A | 9/1981 | Brinkhous et al. |
| 4,298,441 A | 11/1981 | Seidel et al. |
| 4,323,478 A | 4/1982 | Adams et al. |
| 4,324,685 A | 4/1982 | Louderback |
| 4,330,463 A | 5/1982 | Luijerink |
| 4,333,767 A | 6/1982 | Nass |
| 4,337,240 A | 6/1982 | Saklad |
| 4,442,655 A | 4/1984 | Stroetmann |
| 4,456,590 A | 6/1984 | Rubinstein |
| 4,465,774 A | 8/1984 | Huang et al. |
| 4,495,278 A | 1/1985 | Thomas |
| 4,506,455 A | 3/1985 | Rossi |
| 4,543,335 A | 9/1985 | Sommer et al. |
| 4,581,231 A | 4/1986 | Purcell et al. |
| 4,595,021 A | 6/1986 | Shimizu et al. |
| 4,614,795 A | 9/1986 | Chavin et al. |
| 4,624,927 A | 11/1986 | Fukushima et al. |
| 4,650,678 A | 3/1987 | Fuhge et al. |
| 4,664,913 A | 5/1987 | Mielke et al. |
| 4,666,725 A | 5/1987 | Yamashita et al. |
| 4,687,664 A | 8/1987 | Philapitsch et al. |
| 4,716,119 A | 12/1987 | Rehner et al. |
| 4,722,790 A | 2/1988 | Cawley et al. |
| 4,730,460 A | 3/1988 | Coelho et al. |
| 4,731,330 A | 3/1988 | Hill et al. |
| 4,746,730 A | 5/1988 | De Ambrosi et al. |
| 4,780,314 A | 10/1988 | Graves |
| 4,806,343 A | 2/1989 | Carpenter et al. |
| 4,812,557 A | 3/1989 | Yasushi et al. |
| 4,813,210 A | 3/1989 | Masuda et al. |
| 4,850,353 A | 7/1989 | Stasz et al. |
| 4,874,690 A | 10/1989 | Goodrich, Jr. et al. |
| 4,877,608 A | 10/1989 | Lee et al. |
| 4,877,741 A | 10/1989 | Babcock et al. |
| 4,902,287 A | 2/1990 | Carmen et al. |
| 4,904,641 A | 2/1990 | Eibl et al. |
| 4,973,327 A | 11/1990 | Goodrich, Jr. et al. |
| 4,986,998 A | 1/1991 | Yoo et al. |
| 4,994,057 A | 2/1991 | Carmen et al. |
| 5,043,261 A | 8/1991 | Goodrich et al. |
| 5,045,446 A | 9/1991 | Goodrich, Jr. et al. |
| 5,059,036 A | 10/1991 | Richison et al. |
| 5,059,518 A | 10/1991 | Kortright et al. |
| 5,061,789 A | 10/1991 | Moller et al. |
| 5,063,178 A | 11/1991 | Toomey |

(56) References Cited

U.S. PATENT DOCUMENTS

| | | | |
|---|---|---|---|
| 5,073,378 | A | 12/1991 | Shoshan et al. |
| 5,114,004 | A | 5/1992 | Isono et al. |
| 5,118,795 | A | 6/1992 | Rubinstein |
| 5,129,162 | A | 7/1992 | Hemmersbach et al. |
| 5,147,803 | A | 9/1992 | Enomoto |
| 5,151,500 | A | 9/1992 | Wismer-Pedersen et al. |
| 5,171,661 | A | 12/1992 | Goodrich, Jr. et al. |
| 5,178,884 | A | 1/1993 | Goodrich et al. |
| 5,213,814 | A | 5/1993 | Goodrich, Jr. et al. |
| 5,242,792 | A | 9/1993 | Rudolph et al. |
| 5,257,983 | A | 11/1993 | Garyantes et al. |
| 5,260,420 | A | 11/1993 | Burnouf-Radosevich et al. |
| 5,262,325 | A | 11/1993 | Zimmermann et al. |
| 5,304,383 | A | 4/1994 | Eibl et al. |
| 5,309,649 | A | 5/1994 | Bergmann et al. |
| 5,340,592 | A | 8/1994 | Goodrich, Jr. et al. |
| 5,399,670 | A | 3/1995 | Bhattacharya et al. |
| 5,411,893 | A | 5/1995 | Eden et al. |
| 5,420,250 | A | 5/1995 | Lontz |
| 5,425,951 | A | 6/1995 | Goodrich, Jr. et al. |
| 5,464,471 | A | 11/1995 | Whalen et al. |
| 5,514,123 | A | 5/1996 | Adolf et al. |
| 5,514,586 | A | 5/1996 | Hottinger et al. |
| 5,527,260 | A | 6/1996 | Kameyama |
| 5,547,873 | A | 8/1996 | Magneson et al. |
| 5,551,781 | A | 9/1996 | Wilkes et al. |
| 5,585,007 | A | 12/1996 | Antanavich et al. |
| 5,637,345 | A | 6/1997 | Lee et al. |
| 5,648,206 | A | 7/1997 | Goodrich, Jr. et al. |
| 5,651,966 | A | 7/1997 | Read et al. |
| 5,656,498 | A | 8/1997 | Iijima et al. |
| 5,690,963 | A | 11/1997 | Spargo et al. |
| 5,695,764 | A | 12/1997 | Bontemps |
| 5,698,535 | A | 12/1997 | Geczy et al. |
| 5,736,313 | A | 4/1998 | Spargo et al. |
| 5,747,268 | A | 5/1998 | Herring et al. |
| 5,750,330 | A | 5/1998 | Tometsko et al. |
| 5,750,657 | A | 5/1998 | Edwardson et al. |
| 5,759,774 | A | 6/1998 | Hackett et al. |
| 5,795,571 | A | 8/1998 | Cederholm-Williams et al. |
| 5,831,027 | A | 11/1998 | McIntosh et al. |
| 5,834,418 | A | 11/1998 | Brazeau et al. |
| 5,837,519 | A | 11/1998 | Savage et al. |
| 5,849,473 | A | 12/1998 | Cabrera et al. |
| 5,853,388 | A | 12/1998 | Semel |
| 5,860,222 | A | 1/1999 | Leander |
| 5,861,311 | A | 1/1999 | Maples et al. |
| 5,891,393 | A | 4/1999 | Read et al. |
| 5,919,766 | A | 7/1999 | Osterberg et al. |
| 5,919,935 | A | 7/1999 | Platz et al. |
| 5,928,213 | A | 7/1999 | Barney et al. |
| 5,946,931 | A | 9/1999 | Lomax et al. |
| 5,968,831 | A | 10/1999 | Shukla et al. |
| 5,985,582 | A | 11/1999 | Triscott |
| 6,007,529 | A | 12/1999 | Gustafsson et al. |
| 6,034,060 | A | 3/2000 | Yamamoto et al. |
| 6,060,233 | A | 5/2000 | Wiggins |
| 6,132,454 | A | 10/2000 | Fellows |
| 6,139,878 | A | 10/2000 | Summaria et al. |
| 6,148,536 | A | 11/2000 | Iijima |
| 6,187,553 | B1 | 2/2001 | Antignani et al. |
| 6,199,297 | B1 | 3/2001 | Wisniewski |
| 6,218,195 | B1 | 4/2001 | Gottschalk et al. |
| 6,221,575 | B1 | 4/2001 | Roser et al. |
| 6,270,985 | B1 | 8/2001 | Gottschalk et al. |
| 6,323,036 | B1 | 11/2001 | Chapoteau et al. |
| 6,323,037 | B1 | 11/2001 | Lauto et al. |
| 6,331,557 | B1 | 12/2001 | Brugnara et al. |
| 6,346,216 | B1 | 2/2002 | Kent |
| 6,350,584 | B1 | 2/2002 | Gottschalk et al. |
| 6,358,236 | B1 | 3/2002 | DeFoggi et al. |
| 6,358,678 | B1 | 3/2002 | Bakaltcheva et al. |
| 6,372,423 | B1 | 4/2002 | Braun |
| 6,381,870 | B1 | 5/2002 | Kohlman et al. |
| 6,398,771 | B1 | 6/2002 | Gustafsson et al. |
| 6,416,717 | B1 | 7/2002 | Suzuki et al. |
| 6,472,162 | B1 | 10/2002 | Coelho et al. |
| 6,517,526 | B1 | 2/2003 | Tamari |
| 6,566,504 | B2 | 5/2003 | Bhattacharya et al. |
| 6,608,237 | B1 | 8/2003 | Li et al. |
| RE38,431 | E | 2/2004 | Miekka et al. |
| 6,773,425 | B1 | 8/2004 | Tamari |
| 6,852,540 | B2 | 2/2005 | Makiuchi et al. |
| 6,869,901 | B2 | 3/2005 | Lubker, II |
| 6,872,576 | B1 | 3/2005 | McIntyre |
| 6,887,852 | B1 | 5/2005 | Paik et al. |
| 6,890,512 | B2 | 5/2005 | Roser et al. |
| 6,981,337 | B2 | 1/2006 | Jones et al. |
| 7,041,635 | B2 | 5/2006 | Kim et al. |
| 7,048,709 | B2 | 5/2006 | Goudaliez et al. |
| 7,112,320 | B1 | 9/2006 | Beaulieu et al. |
| 7,175,614 | B2 | 2/2007 | Gollier et al. |
| 7,179,951 | B2 | 2/2007 | Krishnaswamy-Mirle et al. |
| 7,202,341 | B2 | 4/2007 | McGinnis et al. |
| 7,249,880 | B2 | 7/2007 | Zambaux |
| 7,343,696 | B2 | 3/2008 | Covert |
| 7,358,039 | B2 | 4/2008 | Fischer et al. |
| 7,363,726 | B2 | 4/2008 | Wang |
| 7,411,038 | B2 | 8/2008 | Haynie |
| 7,422,726 | B2 | 9/2008 | Hammerstedt et al. |
| 7,435,795 | B2 | 10/2008 | McGinnis et al. |
| 7,473,246 | B2 | 1/2009 | Vancaillie et al. |
| 7,480,032 | B2 | 1/2009 | Braig et al. |
| 7,482,020 | B2 | 1/2009 | Hennessy et al. |
| 7,501,493 | B2 | 3/2009 | Roser |
| 7,569,184 | B2 | 8/2009 | Wandell et al. |
| 7,618,406 | B2 | 11/2009 | Roger |
| 7,678,888 | B2 | 3/2010 | Friedman et al. |
| 7,727,743 | B2 | 6/2010 | Bardat et al. |
| 7,776,022 | B2 | 8/2010 | McCarthy et al. |
| 7,811,558 | B2 | 10/2010 | Ho et al. |
| 7,879,332 | B2 | 2/2011 | Zurlo et al. |
| 7,931,919 | B2 | 4/2011 | Bakaltcheva et al. |
| 7,966,746 | B2 | 6/2011 | Py |
| 8,013,022 | B2 | 9/2011 | DeAngelo et al. |
| 8,053,248 | B2 | 11/2011 | Bakaltcheva et al. |
| 8,057,872 | B2 | 11/2011 | Chen |
| 8,097,403 | B2 | 1/2012 | Ho et al. |
| 8,187,475 | B2 | 5/2012 | Hecker et al. |
| 8,235,965 | B2 | 8/2012 | Roger |
| 8,236,355 | B2 | 8/2012 | Eijkenboom |
| 8,268,362 | B2 | 9/2012 | Braun et al. |
| 8,277,837 | B2 | 10/2012 | Fischer et al. |
| 8,313,654 | B2 | 11/2012 | Piazza et al. |
| 8,372,343 | B2 | 2/2013 | Goldstein |
| 8,377,882 | B2 | 2/2013 | Schneider |
| 8,407,912 | B2 | 4/2013 | Hubbard, Jr. et al. |
| 8,430,970 | B2 | 4/2013 | Swami et al. |
| 8,449,520 | B2 | 5/2013 | Pepper et al. |
| 8,491,178 | B2 | 7/2013 | Breidenthal et al. |
| 8,492,081 | B2 | 7/2013 | Nichols et al. |
| 8,512,754 | B2 | 8/2013 | Needham |
| 8,516,714 | B2 | 8/2013 | Biemans et al. |
| 8,518,452 | B2 | 8/2013 | Bjornstrup et al. |
| 8,529,961 | B2 | 9/2013 | Campbell et al. |
| 8,598,319 | B2 | 12/2013 | Michel et al. |
| 8,603,063 | B2 | 12/2013 | Grimm |
| 8,858,681 | B2 * | 10/2014 | Harp .................. B01D 39/1623 95/45 |
| 8,951,565 | B2 | 2/2015 | McCarthy |
| 9,011,846 | B2 | 4/2015 | Overholser et al. |
| 9,046,303 | B2 | 6/2015 | Yagi |
| 9,132,206 | B2 | 9/2015 | McCarthy |
| 9,161,527 | B2 | 10/2015 | Cutting et al. |
| 9,469,835 | B2 | 10/2016 | Bronshtain |
| 9,545,379 | B2 * | 1/2017 | Liu ............. F26B 3/06 |
| 9,561,184 | B2 * | 2/2017 | Khan .............. B01J 19/06 |
| 9,561,893 | B2 | 2/2017 | Root et al. |
| 9,696,284 | B2 | 7/2017 | Rannisto et al. |
| 9,796,273 | B2 | 10/2017 | Ragazzini |
| 9,863,699 | B2 | 1/2018 | Corbin, III et al. |
| 9,863,701 | B2 | 1/2018 | Robinson |
| 10,058,091 | B2 | 8/2018 | Wolf et al. |
| 10,377,520 | B2 | 8/2019 | Root et al. |

(56) References Cited

U.S. PATENT DOCUMENTS

| | | | |
|---|---|---|---|
| 10,492,507 B2 | 12/2019 | Rizvi | |
| 10,507,165 B2* | 12/2019 | Di Naro | A61M 5/1407 |
| 10,539,367 B2 | 1/2020 | Corbin, III et al. | |
| 10,723,497 B2 | 7/2020 | Diaz Guerrero | |
| 10,793,327 B2* | 10/2020 | Weimer | B65D 51/241 |
| 10,830,535 B2 | 11/2020 | Oprins et al. | |
| 10,844,366 B2 | 11/2020 | Durance et al. | |
| 11,236,942 B2 | 2/2022 | Christ | |
| 11,236,943 B2 | 2/2022 | Christ | |
| 2001/0004641 A1 | 6/2001 | Hawkins | |
| 2001/0031721 A1 | 10/2001 | Webb et al. | |
| 2002/0035354 A1 | 3/2002 | Mirle et al. | |
| 2002/0146409 A1 | 10/2002 | Herring et al. | |
| 2003/0065149 A1 | 4/2003 | McGinnis et al. | |
| 2003/0068416 A1 | 4/2003 | Burgess et al. | |
| 2003/0080056 A1 | 5/2003 | Boos et al. | |
| 2003/0104508 A1 | 6/2003 | Gempeler et al. | |
| 2003/0134418 A1 | 7/2003 | Mitaka | |
| 2003/0143566 A1 | 7/2003 | Helftenbein | |
| 2004/0005310 A1 | 1/2004 | Rapp et al. | |
| 2004/0081588 A1 | 4/2004 | Hammerstedt et al. | |
| 2004/0126880 A1 | 7/2004 | Manders et al. | |
| 2004/0132207 A1 | 7/2004 | Arima et al. | |
| 2005/0158856 A1 | 7/2005 | Edelson et al. | |
| 2005/0170068 A1 | 8/2005 | Roodink et al. | |
| 2005/0282734 A1 | 12/2005 | Kadima et al. | |
| 2006/0004189 A1 | 1/2006 | Gandy | |
| 2006/0134084 A1 | 6/2006 | Wolkers et al. | |
| 2006/0182652 A1 | 8/2006 | Burgess et al. | |
| 2006/0216687 A1 | 9/2006 | Alves-Filho et al. | |
| 2006/0263759 A1 | 11/2006 | Alves-Filho et al. | |
| 2007/0014780 A1 | 1/2007 | Woolverton | |
| 2007/0110817 A1 | 5/2007 | Shestakov | |
| 2007/0116599 A1 | 5/2007 | Walters et al. | |
| 2007/0135343 A1 | 6/2007 | Webb et al. | |
| 2007/0166389 A1 | 7/2007 | Bakaltcheva | |
| 2007/0275028 A1 | 11/2007 | Barry et al. | |
| 2008/0038818 A1 | 2/2008 | Natan et al. | |
| 2008/0063697 A1 | 3/2008 | Bedard | |
| 2008/0256822 A1 | 4/2008 | Suzuki et al. | |
| 2008/0119818 A1 | 5/2008 | Bakaltcheva et al. | |
| 2008/0145444 A1 | 6/2008 | Merchant et al. | |
| 2008/0193386 A1 | 8/2008 | Yoo et al. | |
| 2008/0206293 A1 | 8/2008 | Toreki et al. | |
| 2008/0234653 A1 | 9/2008 | McCarthy et al. | |
| 2008/0234654 A1 | 9/2008 | McCarthy et al. | |
| 2008/0249499 A1 | 10/2008 | Vancaillie et al. | |
| 2008/0299212 A1 | 12/2008 | Kim et al. | |
| 2009/0036862 A1 | 2/2009 | Grimm | |
| 2009/0107001 A1 | 4/2009 | McCarthy | |
| 2009/0113753 A1 | 5/2009 | Pepper et al. | |
| 2009/0223080 A1 | 9/2009 | McCarthy et al. | |
| 2009/0324929 A1 | 12/2009 | Yamakawa et al. | |
| 2010/0049156 A1 | 2/2010 | Dickhorner et al. | |
| 2010/0144595 A1 | 6/2010 | Bucci | |
| 2010/0159023 A1 | 6/2010 | Bjornstrup | |
| 2010/0168018 A1 | 7/2010 | Pikal et al. | |
| 2011/0008458 A1 | 1/2011 | Gandy et al. | |
| 2011/0008459 A1 | 1/2011 | Marguerre et al. | |
| 2011/0020299 A1 | 1/2011 | Bader | |
| 2011/0114524 A1 | 5/2011 | Eibl | |
| 2011/0142948 A1 | 6/2011 | Langer et al. | |
| 2011/0144613 A1 | 6/2011 | Pepper et al. | |
| 2011/0177541 A1 | 7/2011 | Martinoli et al. | |
| 2011/0183311 A1 | 7/2011 | Ho et al. | |
| 2011/0263408 A1 | 10/2011 | Suto et al. | |
| 2011/0282325 A1 | 11/2011 | Gregory | |
| 2012/0027867 A1 | 2/2012 | Fischer et al. | |
| 2012/0040384 A1 | 2/2012 | Stangier | |
| 2012/0045518 A1 | 2/2012 | Nielsen et al. | |
| 2012/0070855 A1 | 3/2012 | Mirshahi et al. | |
| 2012/0141595 A1 | 6/2012 | Tseng et al. | |
| 2012/0156306 A1 | 6/2012 | Weissman et al. | |
| 2012/0231485 A1 | 9/2012 | Önundarson et al. | |
| 2012/0252044 A1 | 10/2012 | Rechner et al. | |
| 2012/0329082 A1 | 12/2012 | Viola et al. | |
| 2013/0008048 A1 | 1/2013 | Patel et al. | |
| 2013/0019572 A1 | 1/2013 | Beator et al. | |
| 2013/0030161 A1 | 1/2013 | Anitua Aldecoa | |
| 2013/0040890 A1 | 2/2013 | Guo et al. | |
| 2013/0090291 A1 | 4/2013 | Guile et al. | |
| 2013/0116410 A1 | 5/2013 | Ivarsson et al. | |
| 2013/0122107 A1 | 5/2013 | Bakaltcheva | |
| 2013/0126370 A1 | 5/2013 | DiLiberto et al. | |
| 2013/0143198 A1 | 6/2013 | Sailliol | |
| 2013/0149727 A1 | 6/2013 | Aygen | |
| 2013/0183661 A1 | 7/2013 | Prante et al. | |
| 2013/0195897 A1 | 8/2013 | Teschner et al. | |
| 2013/0195959 A1 | 8/2013 | Patel | |
| 2013/0202585 A1 | 8/2013 | Bardat et al. | |
| 2013/0243877 A1 | 9/2013 | Haley et al. | |
| 2013/0251695 A1 | 9/2013 | Farmer et al. | |
| 2013/0303842 A1 | 11/2013 | Zeitels et al. | |
| 2013/0316011 A1 | 11/2013 | Ahn et al. | |
| 2013/0326899 A1 | 12/2013 | Yagi | |
| 2014/0178513 A1 | 6/2014 | Matthews | |
| 2014/0212895 A1 | 7/2014 | Lim | |
| 2014/0259724 A1 | 9/2014 | McCarthy et al. | |
| 2014/0287643 A1 | 9/2014 | Nozaki et al. | |
| 2014/0360891 A1 | 12/2014 | Kline et al. | |
| 2015/0158652 A1 | 6/2015 | Root et al. | |
| 2015/0354894 A1 | 12/2015 | Corbin, III et al. | |
| 2016/0084572 A1* | 3/2016 | Khan | F26B 3/12 |
| | | | 34/381 |
| 2016/0375184 A1 | 12/2016 | Albert et al. | |
| 2017/0100339 A1* | 4/2017 | Liu | A61K 9/1688 |
| 2017/0113824 A1 | 4/2017 | Root et al. | |
| 2017/0203871 A1 | 7/2017 | Murto et al. | |
| 2017/0258877 A1 | 9/2017 | Bare et al. | |
| 2017/0259186 A1* | 9/2017 | Khan | B01J 2/04 |
| 2017/0367322 A1 | 12/2017 | Liu et al. | |
| 2018/0128544 A1 | 5/2018 | Corbin, III et al. | |
| 2018/0221418 A1 | 8/2018 | Daniel et al. | |
| 2019/0000979 A1 | 1/2019 | Cleek et al. | |
| 2019/0030169 A1 | 1/2019 | Ivarsson et al. | |
| 2019/0106254 A1* | 4/2019 | Weimer | A01N 1/0263 |
| 2019/0142694 A1 | 5/2019 | Di Naro | |
| 2020/0253826 A1 | 8/2020 | Qiu et al. | |
| 2020/0288703 A1* | 9/2020 | Parakininkas | A01N 1/0284 |
| 2020/0289728 A1* | 9/2020 | Johnson | F26B 5/06 |
| 2020/0292231 A1* | 9/2020 | Johnson | A01N 1/0252 |
| 2021/0016943 A1* | 1/2021 | Weimer | B65D 51/241 |
| 2021/0127663 A1 | 5/2021 | Paukkonen | |

FOREIGN PATENT DOCUMENTS

| | | |
|---|---|---|
| AU | 622133 B2 | 4/1992 |
| AU | 8165698 A | 1/2000 |
| AU | 744025 B2 | 2/2002 |
| AU | 2002326819 A1 | 4/2003 |
| AU | 2007205748 B2 | 11/2009 |
| AU | 2012205238 A1 | 8/2012 |
| BG | 64922 B1 | 9/2006 |
| CA | 745958 A | 11/1966 |
| CA | 780792 A | 3/1968 |
| CA | 787838 A | 6/1968 |
| CA | 835939 A | 3/1970 |
| CA | 843883 A | 6/1970 |
| CA | 1260389 A | 9/1989 |
| CN | 1210267 A | 3/1999 |
| CN | 1242429 A | 1/2000 |
| CN | 1376520 A | 10/2002 |
| CN | 1410537 A | 4/2003 |
| CN | 1156282 C | 7/2004 |
| CN | 1157194 C | 7/2004 |
| CN | 1162160 C | 8/2004 |
| CN | 1187616 C | 2/2005 |
| CN | 1220512 C | 9/2005 |
| CN | 1745627 A | 3/2006 |
| CN | 1250718 C | 4/2006 |
| CN | 1267340 C | 8/2006 |
| CN | 1270731 C | 8/2006 |
| CN | 1281161 C | 10/2006 |
| CN | 1931025 A | 3/2007 |

(56) References Cited

FOREIGN PATENT DOCUMENTS

| | | |
|---|---|---|
| CN | 101152211 A | 4/2008 |
| CN | 101216432 A | 7/2008 |
| CN | 101299029 A | 11/2008 |
| CN | 101310728 A | 11/2008 |
| CN | 100469359 C | 3/2009 |
| CN | 101416985 A | 4/2009 |
| CN | 100531723 C | 8/2009 |
| CN | 101579356 A | 11/2009 |
| CN | 100584942 C | 1/2010 |
| CN | 101618120 A | 1/2010 |
| CN | 101167745 B | 6/2010 |
| CN | 101766252 A | 7/2010 |
| CN | 101833009 A | 9/2010 |
| CN | 101879333 A | 11/2010 |
| CN | 101893628 A | 11/2010 |
| CN | 101893639 A | 11/2010 |
| CN | 101957364 A | 1/2011 |
| CN | 101971972 A | 2/2011 |
| CN | 101347617 B | 4/2011 |
| CN | 102000022 A | 4/2011 |
| CN | 102008504 A | 4/2011 |
| CN | 102012433 A | 4/2011 |
| CN | 102050876 A | 5/2011 |
| CN | 102078306 A | 6/2011 |
| CN | 102106872 A | 6/2011 |
| CN | 101433553 B | 8/2011 |
| CN | 102207504 A | 10/2011 |
| CN | 101385855 B | 11/2011 |
| CN | 102229670 A | 11/2011 |
| CN | 102241767 A | 11/2011 |
| CN | 102250238 A | 11/2011 |
| CN | 101461939 B | 1/2012 |
| CN | 102337252 A | 2/2012 |
| CN | 102363634 A | 2/2012 |
| CN | 102426240 A | 4/2012 |
| CN | 102426258 A | 4/2012 |
| CN | 101285086 B | 5/2012 |
| CN | 102435743 A | 5/2012 |
| CN | 101830979 B | 6/2012 |
| CN | 101843335 B | 6/2012 |
| CN | 102507934 A | 6/2012 |
| CN | 102512418 A | 6/2012 |
| CN | 102524812 A | 7/2012 |
| CN | 102552154 A | 7/2012 |
| CN | 102579737 A | 7/2012 |
| CN | 102590496 A | 7/2012 |
| CN | 102590529 A | 7/2012 |
| CN | 102600074 A | 7/2012 |
| CN | 102600231 A | 7/2012 |
| CN | 102600508 A | 7/2012 |
| CN | 101899110 B | 8/2012 |
| CN | 102614219 A | 8/2012 |
| CN | 102628869 A | 8/2012 |
| CN | 102645358 A | 8/2012 |
| CN | 101816789 B | 9/2012 |
| CN | 102688200 A | 9/2012 |
| CN | 102692514 A | 9/2012 |
| CN | 101900712 B | 10/2012 |
| CN | 102327289 B | 10/2012 |
| CN | 102697581 A | 10/2012 |
| CN | 102746396 A | 10/2012 |
| CN | 102754848 A | 10/2012 |
| CN | 102327288 B | 11/2012 |
| CN | 102793053 A | 11/2012 |
| CN | 101843289 B | 12/2012 |
| CN | 102854322 A | 1/2013 |
| CN | 102866220 A | 1/2013 |
| CN | 102866255 A | 1/2013 |
| CN | 102879560 A | 1/2013 |
| CN | 101948630 B | 2/2013 |
| CN | 102908321 A | 2/2013 |
| CN | 102908368 A | 2/2013 |
| CN | 102093385 B | 3/2013 |
| CN | 102228683 B | 3/2013 |
| CN | 102240310 B | 3/2013 |
| CN | 102988974 A | 3/2013 |
| CN | 102210854 B | 4/2013 |
| CN | 103007280 A | 4/2013 |
| CN | 103039693 A | 4/2013 |
| CN | 103054816 A | 4/2013 |
| CN | 101756013 B | 5/2013 |
| CN | 103076455 A | 5/2013 |
| CN | 103113456 A | 5/2013 |
| CN | 102258780 B | 6/2013 |
| CN | 102319425 B | 6/2013 |
| CN | 102525954 B | 6/2013 |
| CN | 102274493 B | 8/2013 |
| CN | 203572189 U | 4/2014 |
| CN | 106461327 | 2/2017 |
| CS | 277138 B6 | 11/1992 |
| DE | 109659 A1 | 11/1974 |
| DE | 2430447 A1 | 1/1975 |
| DE | 112775 A1 | 5/1975 |
| DE | 2617742 | 6/1977 |
| DE | 2365629 C2 | 6/1983 |
| DE | 19729778 A1 | 1/1999 |
| DE | 69521470 T2 | 5/2002 |
| DE | 69133198 T2 | 7/2003 |
| DE | 69810755 T2 | 8/2003 |
| EP | 105923 A1 | 4/1984 |
| EP | 121868 A1 | 10/1984 |
| EP | 0157579 A2 | 10/1985 |
| EP | 111777 B1 | 3/1987 |
| EP | 0124018 B1 | 11/1987 |
| EP | 204045 A3 | 1/1988 |
| EP | 0284249 A1 | 9/1988 |
| EP | 0335682 A1 | 10/1989 |
| EP | 0343596 B1 | 11/1989 |
| EP | 206448 B1 | 11/1990 |
| EP | 215050 B1 | 2/1991 |
| EP | 445108 A1 | 9/1991 |
| EP | 392377 B1 | 2/1995 |
| EP | 593176 A3 | 3/1995 |
| EP | 2729932 A1 | 8/1996 |
| EP | 752097 A1 | 1/1997 |
| EP | 485377 B1 | 5/1999 |
| EP | 1021726 A1 | 7/2000 |
| EP | 1171163 A1 | 1/2002 |
| EP | 1243275 A1 | 9/2002 |
| EP | 1286706 A2 | 3/2003 |
| EP | 876155 B1 | 7/2004 |
| EP | 1087990 B1 | 9/2004 |
| EP | 1113269 B1 | 10/2006 |
| EP | 1870649 A1 | 12/2007 |
| EP | 997735 B1 | 1/2008 |
| EP | 1958618 A1 | 8/2008 |
| EP | 1730299 B1 | 6/2011 |
| EP | 2371343 A3 | 12/2011 |
| EP | 2431024 A1 | 3/2012 |
| EP | 2564481 | 3/2013 |
| EP | 2574350 A1 | 4/2013 |
| EP | 1407780 B1 | 5/2013 |
| EP | 3290064 A1 | 3/2018 |
| FR | 2001727 A1 | 10/1969 |
| FR | 2160285 A1 | 6/1973 |
| FR | 2187909 A1 | 1/1974 |
| FR | 2224118 A1 | 10/1974 |
| FR | 2227276 A1 | 11/1974 |
| FR | 2363577 A1 | 3/1978 |
| FR | 2475737 A1 | 8/1981 |
| FR | 2600998 A1 | 1/1988 |
| FR | 2717782 A1 | 9/1995 |
| FR | 2729932 | 8/1996 |
| FR | 2729932 A1 | 8/1996 |
| FR | 2814239 A1 | 3/2002 |
| FR | 2963556 A3 | 2/2012 |
| GB | 353286 A | 7/1931 |
| GB | 425567 A | 3/1935 |
| GB | 450146 A | 7/1936 |
| GB | 491515 A | 9/1938 |
| GB | 620573 A | 3/1949 |
| GB | 727148 A | 3/1955 |
| GB | 731104 A | 6/1955 |
| GB | 748784 A | 5/1956 |

(56) References Cited

FOREIGN PATENT DOCUMENTS

| | | |
|---|---|---|
| GB | 770075 A | 3/1957 |
| GB | 807781 A | 1/1959 |
| GB | 814491 A | 6/1959 |
| GB | 853288 A | 11/1960 |
| GB | 859609 A | 1/1961 |
| GB | 906860 A | 9/1962 |
| GB | 911181 A | 11/1962 |
| GB | 917012 A | 1/1963 |
| GB | 941019 A | 11/1963 |
| GB | 979759 A | 1/1965 |
| GB | 1003748 A | 9/1965 |
| GB | 1073172 A | 6/1967 |
| GB | 1074461 A | 7/1967 |
| GB | 1186544 A | 4/1970 |
| GB | 1206033 A | 9/1970 |
| GB | 1222810 A | 2/1971 |
| GB | 1266274 A | 3/1972 |
| GB | 1337178 A | 11/1973 |
| GB | 1372812 A | 11/1974 |
| GB | 1391746 A | 4/1975 |
| GB | 1480092 A | 7/1977 |
| GB | 1486787 A | 9/1977 |
| GB | 1497517 A | 1/1978 |
| GB | 1507435 A | 4/1978 |
| GB | 1524712 A | 9/1978 |
| GB | 1530748 A | 11/1978 |
| GB | 1536725 A | 12/1978 |
| GB | 1551792 A | 8/1979 |
| GB | 1551928 A | 9/1979 |
| GB | 1563839 A | 4/1980 |
| GB | 2148090 B | 7/1987 |
| GB | 2167856 B | 12/1988 |
| GB | 2564481 A | 1/2019 |
| IT | 1064142 B | 2/1985 |
| JP | S52156921 A | 12/1977 |
| JP | S53091117 A | 8/1978 |
| JP | S5426961 A | 2/1979 |
| JP | S5571452 A | 5/1980 |
| JP | S56127307 A | 10/1981 |
| JP | S56127308 A | 10/1981 |
| JP | S56160991 A | 12/1981 |
| JP | S5772911 A | 5/1982 |
| JP | S57122796 A | 7/1982 |
| JP | S57142561 A | 9/1982 |
| JP | S57159561 A | 10/1982 |
| JP | S58131566 A | 8/1983 |
| JP | S59088042 A | 5/1984 |
| JP | S59136657 A | 8/1984 |
| JP | S59181224 A | 10/1984 |
| JP | S59212768 A | 12/1984 |
| JP | S59218960 A | 12/1984 |
| JP | S60168051 A | 8/1985 |
| JP | S61040752 A | 2/1986 |
| JP | S61053567 A | 3/1986 |
| JP | S61128974 A | 6/1986 |
| JP | S61155332 A | 7/1986 |
| JP | S61225652 A | 10/1986 |
| JP | S61282054 A | 12/1986 |
| JP | S62010019 A | 1/1987 |
| JP | S62138433 A | 6/1987 |
| JP | H63-036828 A | 2/1988 |
| JP | S63157936 A | 6/1988 |
| JP | 1021741 B | 4/1989 |
| JP | H1247060 A | 10/1989 |
| JP | H2221859 A | 9/1990 |
| JP | H07270405 A | 10/1995 |
| JP | H09020687 A | 1/1997 |
| JP | H09222427 A | 8/1997 |
| JP | 2657092 B2 | 9/1997 |
| JP | H1045616 A | 2/1998 |
| JP | H10108907 A | 4/1998 |
| JP | H10165480 A | 6/1998 |
| JP | 3140797 B2 | 3/2001 |
| JP | 3142192 B2 | 3/2001 |
| JP | 3219181 B2 | 10/2001 |
| JP | 2002029977 A | 1/2002 |
| JP | 2002052067 A | 2/2002 |
| JP | 3292760 B2 | 6/2002 |
| JP | 3365091 B2 | 1/2003 |
| JP | 2003055256 A | 2/2003 |
| JP | 2003055257 A | 2/2003 |
| JP | 2003144523 A | 5/2003 |
| JP | 2003339346 A | 12/2003 |
| JP | 2004049493 A | 2/2004 |
| JP | 3543144 B2 | 7/2004 |
| JP | 3712989 B2 | 11/2005 |
| JP | 2006036749 A | 2/2006 |
| JP | 2007197353 A | 8/2007 |
| JP | 4024506 B2 | 12/2007 |
| JP | 4059299 B2 | 3/2008 |
| JP | 2006545011 | 5/2008 |
| JP | 2008527741 A | 7/2008 |
| JP | 2009297212 A | 12/2009 |
| JP | 2010266086 A | 11/2010 |
| JP | 2011239 A | 1/2011 |
| JP | 2011120763 A | 6/2011 |
| JP | 2012051895 A | 3/2012 |
| JP | 5002106 B2 | 8/2012 |
| JP | 5037621 B2 | 10/2012 |
| JP | 5049447 B2 | 10/2012 |
| JP | 5087815 B2 | 12/2012 |
| JP | 5252909 B2 | 7/2013 |
| JP | 5340945 B2 | 11/2013 |
| JP | 2014-028661 | 2/2014 |
| JP | 5960660 B2 | 8/2016 |
| JP | 2017-517335 | 6/2017 |
| JP | 6219922 B2 | 10/2017 |
| JP | 6305870 B2 | 4/2018 |
| KR | 100197297 B1 | 6/1999 |
| KR | 20000020804 A | 4/2000 |
| KR | 100503629 B1 | 7/2005 |
| KR | 20060005770 A | 1/2006 |
| KR | 100631188 B1 | 10/2006 |
| KR | 100767541 B1 | 10/2007 |
| KR | 100857273 B1 | 9/2008 |
| KR | 100908742 B1 | 7/2009 |
| KR | 20110008382 A | 1/2011 |
| KR | 101157096 B1 | 6/2012 |
| KR | 101200423 B1 | 11/2012 |
| KR | 20130009161 A | 1/2013 |
| KR | 20130034991 A | 4/2013 |
| KR | 20130053609 A | 5/2013 |
| RU | 2011202 C1 | 4/1994 |
| RU | 2028130 C1 | 2/1995 |
| RU | 2028133 C1 | 2/1995 |
| RU | 2080865 C1 | 6/1997 |
| RU | 2090165 C1 | 9/1997 |
| RU | 2090166 C1 | 9/1997 |
| RU | 2121364 C1 | 11/1998 |
| RU | 2193868 C2 | 12/2002 |
| RU | 2197267 C1 | 1/2003 |
| RU | 2242759 C1 | 12/2004 |
| RU | 2266542 C1 | 12/2005 |
| RU | 2273026 C1 | 3/2006 |
| RU | 2314527 C1 | 1/2008 |
| RU | 2322243 C1 | 4/2008 |
| RU | 2332666 C1 | 8/2008 |
| RU | 2325655 C9 | 11/2008 |
| RU | 2357252 C1 | 5/2009 |
| RU | 2426548 C2 | 8/2011 |
| RU | 2442984 C1 | 2/2012 |
| RU | 2455014 C1 | 7/2012 |
| RU | 2456602 C1 | 7/2012 |
| RU | 2463063 C1 | 10/2012 |
| RU | 2012137892 A | 2/2013 |
| RU | 2478958 C1 | 4/2013 |
| RU | 2492867 C1 | 9/2013 |
| SU | 548275 A1 | 2/1977 |
| SU | 654238 A1 | 3/1979 |
| SU | 686732 A1 | 9/1979 |
| SU | 700129 A1 | 11/1979 |
| SU | 786954 A1 | 12/1980 |
| SU | 1344354 A1 | 10/1987 |
| SU | 1592717 A1 | 9/1990 |

(56) References Cited

FOREIGN PATENT DOCUMENTS

| | | |
|---|---|---|
| SU | 1678371 A1 | 9/1991 |
| SU | 1716443 A1 | 2/1992 |
| SU | 1752187 A3 | 7/1992 |
| TW | 200600103 A | 1/2006 |
| TW | I358264 B | 2/2012 |
| UA | 26543 U | 9/2007 |
| WO | WO-1992013495 A1 | 8/1992 |
| WO | WO-1992014360 A1 | 9/1992 |
| WO | WO-1995012127 A1 | 5/1995 |
| WO | WO-1995015763 A1 | 6/1995 |
| WO | 95/27180 A1 | 10/1995 |
| WO | 96/29556 A1 | 9/1996 |
| WO | 96/31748 A1 | 10/1996 |
| WO | WO-1997046883 A1 | 12/1997 |
| WO | 00/36353 A1 | 6/2000 |
| WO | WO-2000047187 A1 | 8/2000 |
| WO | WO-2001064228 A1 | 9/2001 |
| WO | WO-2002083157 A1 | 10/2002 |
| WO | WO-2002083737 A1 | 10/2002 |
| WO | WO-2002087540 A1 | 11/2002 |
| WO | WO-2003082310 A1 | 10/2003 |
| WO | 2005089816 A1 | 9/2005 |
| WO | 2006000422 A1 | 1/2006 |
| WO | 2006028648 A2 | 3/2006 |
| WO | WO-2006054519 A1 | 5/2006 |
| WO | 2006028648 A3 | 1/2007 |
| WO | 2007104760 A2 | 9/2007 |
| WO | 2008115548 A2 | 9/2008 |
| WO | WO-2008108549 A1 | 9/2008 |
| WO | 2008130602 A1 | 10/2008 |
| WO | 2010019217 A1 | 2/2010 |
| WO | 2010033169 A1 | 3/2010 |
| WO | 2010093429 A1 | 8/2010 |
| WO | WO-2012092712 A1 | 7/2012 |
| WO | WO-2012098358 A1 | 7/2012 |
| WO | WO-2012101109 A1 | 8/2012 |
| WO | WO-2012140209 A1 | 10/2012 |
| WO | WO-2012159075 A1 | 11/2012 |
| WO | WO-2013013537 A1 | 1/2013 |
| WO | WO-2013042868 A1 | 3/2013 |
| WO | WO-2013057219 A1 | 4/2013 |
| WO | 2013062479 A1 | 5/2013 |
| WO | WO-2013076507 A2 | 5/2013 |
| WO | WO-2013085502 A1 | 6/2013 |
| WO | 2014033228 A1 | 3/2014 |
| WO | 2014165222 A1 | 10/2014 |
| WO | 2015191599 A2 | 12/2015 |
| WO | 2015191599 A3 | 4/2016 |
| WO | 2019074886 A1 | 4/2019 |
| WO | WO-2019074886 A1 * 4/2019 | ........... A01N 1/0284 |
| WO | WO-2020185909 A3 * 12/2020 | ........... A01N 1/0263 |
| WO | WO-2020242552 A1 * 12/2020 | .............. F26B 5/044 |

OTHER PUBLICATIONS

Cannon, Jeremy W. M.D., "Prehospital Damage-Control Resuscitation", The New England Journal of Medicine, Jul. 26, 2018, pp. 387-388.

Cherry, Chris, "Containment systems for freeze-drying," ISL-FD, Sep. 7, 2015.

Cherry, Christopher Lee Albert, "Development of Novel Containment Systems for Freeze-Drying," a thesis submitted to Cardiff Metropolitan University, Apr. 10, 2013.

Glassberg et al, "Freeze-dried Plasma at the Point of Injury: from Concept to Doctrine", SHOCK, Dec. 2013, vol. 40, No. 6, pp. 444-450.

Pan et al, "Study of Banana Dehydration Using Sequential Infrared Radiation Heating and Freeze-Drying", LWT—Food Science and Technology, 2008 v. 41, pp. 1944-1951.

Soares, Jeffrey M., "Saving Lives with Freeze-dried Plasma", The United States Army, Nov. 27, 2017, pp. 1-5. https://www.army.mil/article/197409.

Sperry et al, "Prehospital Plasma during Air Medical Transport in Trauma Patients at Risk for Hemorrhagic Shock", The New England Journal of Medicine, Jul. 26, 2018, pp. 315-326.

International Search Report and Written Opinion, PCT/US2020/022113, dated Nov. 5, 2020.

International Search Report and Written Opinion, PCT/US2020/022120, dated Nov. 26, 2020.

International Search Report and Written Opinion, PCT/US2020/022128, dated Sep. 4, 2020.

Invitation to Pay Additional Fee and Partial International Search Report and Written Opinion, PCT/US2020/022120, dated Oct. 1, 2020.

Official Action (with English translation) for China Patent Application No. 201880064085.6, dated Jul. 15, 2021, 12 pages.

International Search Report and Written Opinion for International (PCT) Patent Application No. PCT/US2018/054943, dated Jan. 25, 2019, 14 pages.

Official Action for Canada Patent Application No. 3078625, dated Jul. 16, 2021, 3 pages.

Official Action (with English translation) for Japan Patent Application No. 2020-540696, dated Aug. 24, 2021, 17 pages.

Official Action for U.S. Appl. No. 16/154,976, dated Dec. 20, 2019, 12 pages.

Official Action for U.S. Appl. No. 16/154,976, dated Apr. 13, 2020, 9 pages.

Notice of Allowance for U.S. Appl. No. 16/154,976, dated Jun. 12, 2020, 9 pages.

Official Action for U.S. Appl. No. 17/010,083, dated Jul. 28, 2021, 7 pages.

Notice of Allowance for U.S. Appl. No. 17/010,083, dated Nov. 24, 2021, 6 pages.

Updated Notice of Allowance for U.S. Appl. No. 17/010,083, dated Dec. 19, 2021, 2 pages.

Official Action (with English abstract) for Chinese Patent Application No. 201880064085.6, dated Mar. 11, 2022, 9 pages.

Official Action (with English translation) for Japan Patent Application No. 2020-540696, dated Jan. 11, 2022, 16 pages.

Notice of Allowance for U.S. Appl. No. 17/010,083, dated Feb. 3, 2022, 6 pages.

Official Action for U.S. Appl. No. 16/815,904, dated Feb. 7, 2022, 13 pages.

* cited by examiner

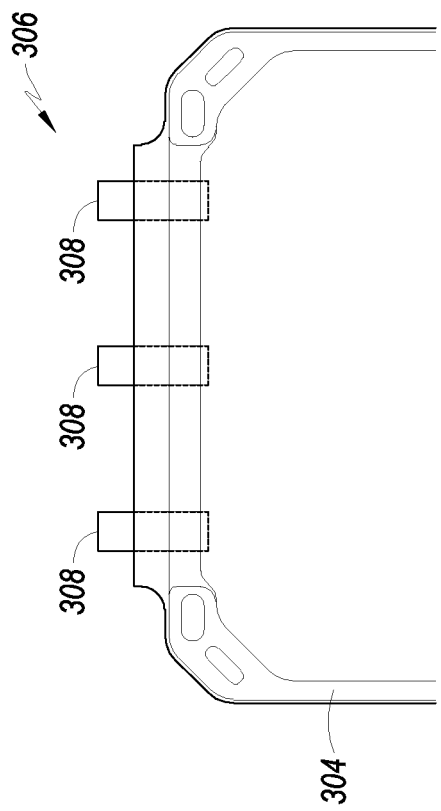
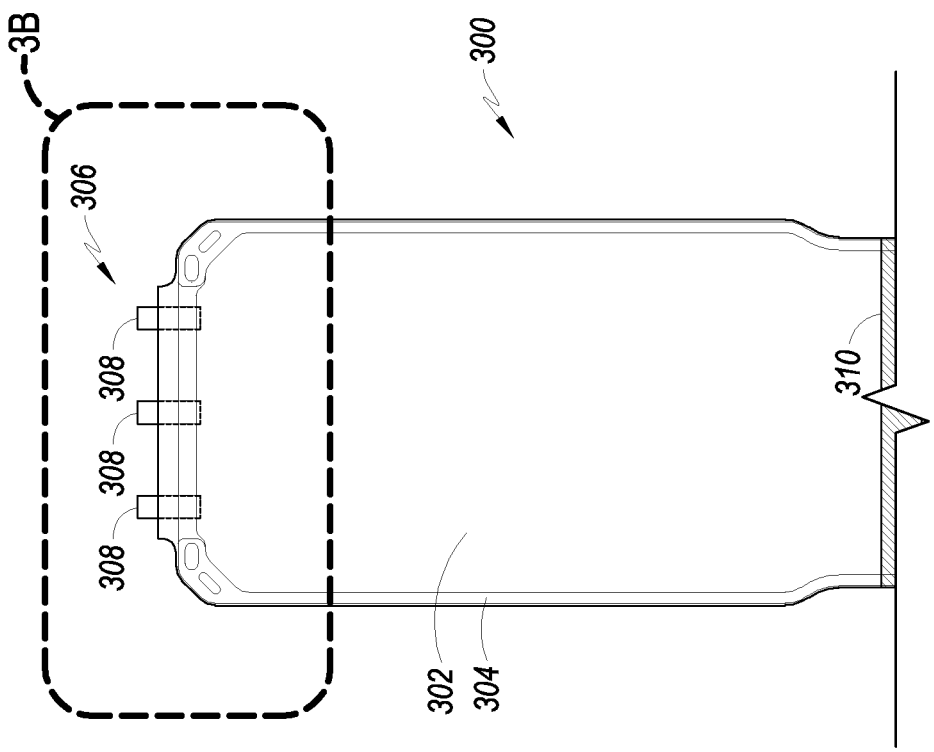

MULTI-PART LYOPHILIZATION CONTAINER AND METHOD OF USE

CROSS-REFERENCE TO RELATED APPLICATIONS

This application claims priority to U.S. Provisional Patent Application No. 62/818,214, entitled "Multi-part Lyophilization Container and Method of Use," filed in the U.S. Patent and Trademark Office on Mar. 14, 2019, U.S. Provisional Patent Application No. 62/952,752, entitled "Lyophilization Loading Tray Assembly and System," filed in the U.S. Patent and Trademark Office on Dec. 23, 2019 and Provisional Patent Application No. 62/971,072, entitled "Lyophilization Container Fill Fixture, System and Method of Use," filed in the U.S. Patent and Trademark Office on Feb. 6, 2020, each of which is incorporated by reference herein in its entirety.

The invention was made with government support under contract number H92222-16-C-0081 awarded by the United States Department of Defense. The government has certain rights in the invention.

BACKGROUND

The present application describes a device and related system and method for lyophilizing and storing a fluid. The device is a continually evolving, multi-section lyophilization container including a peelable seal. The container evolves throughout the stages of filling, lyophilization, storage, reconstitution and infusion. The method describes the manipulation of the container throughout the lyophilization process.

Any suitable fluid may be lyophilized and stored using the devices and techniques described in this disclosure, including human and animal blood and related blood products, such as blood plasma.

Many lyophilization containers and associated techniques are known in the art. Many of these containers and techniques include a breathable membrane and are resultantly vulnerable to a reduction in container performance if the breathable membrane becomes compromised. When lyophilizing human or animal blood, or a component thereof, membrane fouling and an associated diminution in container performance can occur if there is direct contact between the blood and breathable membrane material. Accordingly, various lyophilization techniques and devices have been devised which maintain a separation between the breathable membrane material and blood plasma. For example, one approach utilizes a flexible lyophilization container incorporating a semi-rigid columnar member within the container cavity. When the container is horizontally disposed on a lyophilizer shelf, the columnar member extends upward creating a support which maintains a framed piece of breathable membrane above the liquid plasma. Another approach utilizes a rigid lyophilization tray including a breathable roof. The rigidity of container components causes the roof to be maintained above the plasma throughout lyophilization.

Notably, these techniques are vulnerable to operator error. That is, an inadvertent tilting of the container during pre-load or while in transport may result in membrane fouling. Moreover, these techniques require relatively expensive disposable equipment. Accordingly, there exists a need for an improvement in lyophilization container design.

Although specific embodiments of the present application are provided in view of these and other considerations, the specific problems discussed herein should not be interpreted as limiting the applicability of the embodiments of this disclosure in any way.

SUMMARY

The lyophilization container of the present application describes improvements upon previous container configurations by using a peelable seal in a peelable container region to create an initial occlusion in the container resulting in the isolation of a subject liquid (e.g., blood plasma) in only a non-breathable container section prior to freezing.

This summary is provided to introduce aspects of some embodiments of the present application in a simplified form and is not intended to comprise an exhaustive list of all critical or essential elements of the claimed invention, nor is it intended to limit the scope of the claims.

Embodiments provide for a multi-part lyophilization container. The container includes a front surface, a back surface, a non-breathable section including a port region, a breathable section including a breathable membrane, and a peelable region including a peelable seal encompassing a boundary bridging the non-breathable section and the breathable section. The non-breathable section is configured to accommodate any of a liquid, a solid and a gas, whereas the breathable section is configured to accommodate only a gas.

In another aspect, provided is a method of lyophilizing a fluid in a multi-part container. The method includes inputting a fluid into a non-breathable section of the container, freezing the fluid, applying, in a lyophilization chamber, vacuum pressure, opening the peelable seal using a pressure differential, applying heat energy, sublimating the fluid and creating a temporary occlusion in a peelable region of the container.

In yet another aspect, provided is a method of manufacturing a peelable seal in a multipart lyophilization container. The method includes applying heating elements of a heat-sealing machine to opposing materials of the container at a continuous temperature of approximately 64° C. for approximately 40 seconds.

Further embodiments of the present application include additional devices, methods and systems for lyophilizing fluids. The fluid may be any suitable liquid, including human or animal plasma.

BRIEF DESCRIPTION OF THE DRAWINGS

Non-limiting and non-exhaustive embodiments are described with reference to the following figures.

FIG. 3A is a plan view of a non-breathable section of a lyophilization container according to an embodiment of the present application;

FIG. 3B is an expanded view of the port region of the non-breathable section of the lyophilization container of FIG. 3A;

DETAILED DESCRIPTION

The principles described in the present application may be further understood by reference to the following detailed description and the embodiments depicted in the accompanying drawings. Although specific features are shown and described below with respect to particular embodiments, the present application is not limited to the specific features or embodiments provided. Moreover, embodiments below may be described in connection with the lyophilization and storage of human or animal blood or a component thereof; however, such descriptions are merely illustrative. For example, embodiments may be utilized in connection with blood plasma, a fluid including cryoprecipitate, a fluid including lysed platelets or a cell suspension, but are not limited thereto. Those of skill in the art will appreciate that embodiments of this disclosure may be used in connection with the lyophilization of any suitable fluid or liquid or component thereof.

Embodiments of the present application refer to a closed, sterile container, including sterile fluid pathways, for lyophilizing and storing a fluid. Embodiments described in this application may be implemented in conjunction with many conventional, commercially available lyophilizers, including a Magnum® lyophilizer by Millrock Technology, Inc. Further advantages of the various enumerated embodiments are noted throughout this disclosure.

The terms "multi-part container," "container," "lyophilization container," "multi-part lyophilization container," and the like, are used interchangeably throughout this disclosure. Similarly, the term "breathable," with respect to materials and membranes, may be used interchangeably with the term "semi-permeable," whereas the term "non-breathable" may be used interchangeably with the term "non-permeable." The term "peelable seal" may be used interchangeably with the term "peel seal."

Figure 1:
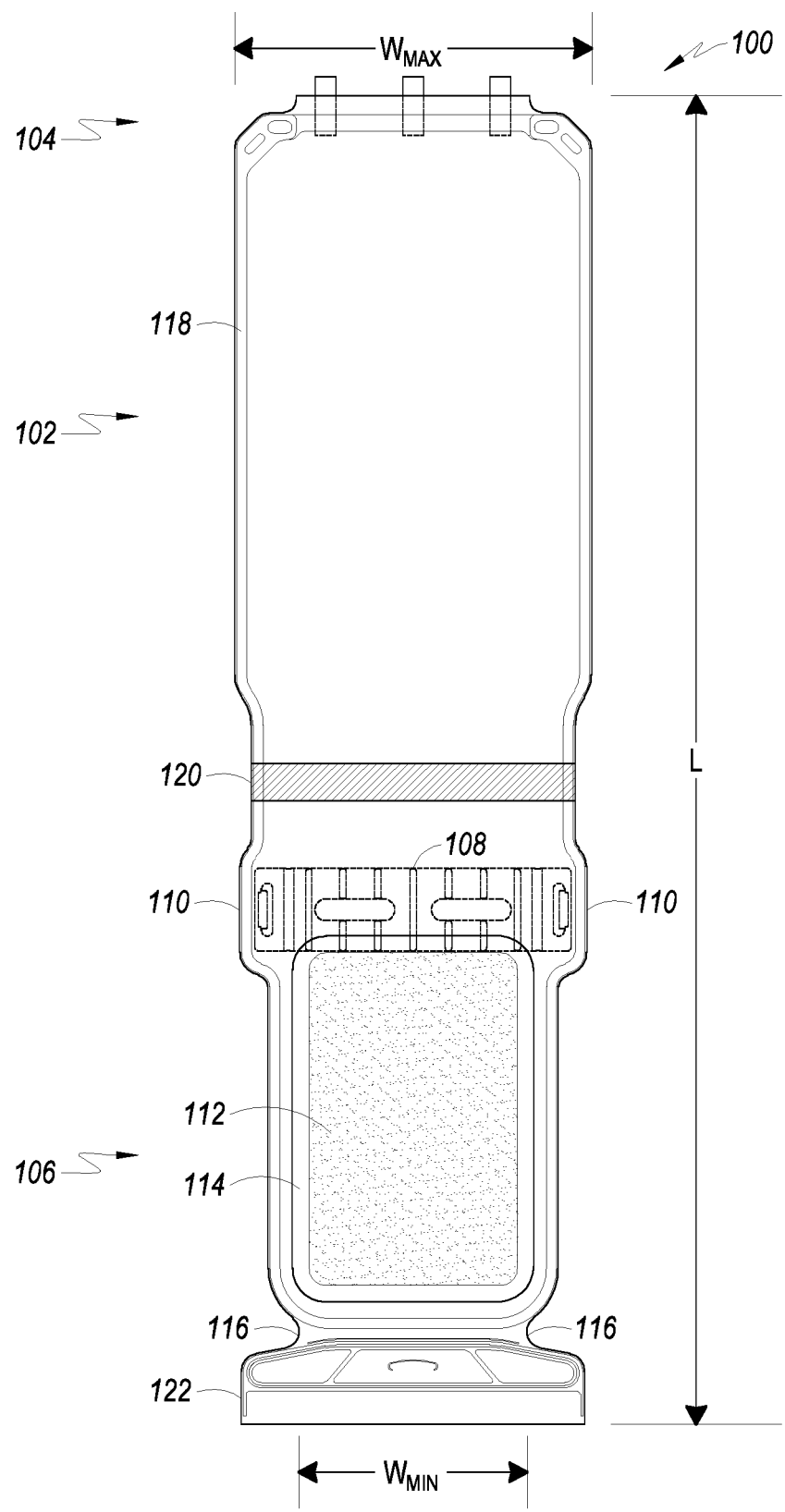
FIG. 1 is a plan view of a lyophilization container according to an embodiment of the present application.

FIG. 1 is plan view of a lyophilization container according to an embodiment of the present application.

Referring to FIG. 1, the lyophilization container 100 includes a non-breathable section 102, including a port region 104; a breathable section 106, including a Hold Open Device (HOD) 108, HOD capture zones 110, a breathable membrane 112, an inner membrane weld 114 and handle recesses 116; an outer perimeter weld 118; a peelable region 120 and a tear-away tail 122.

Figure 7:
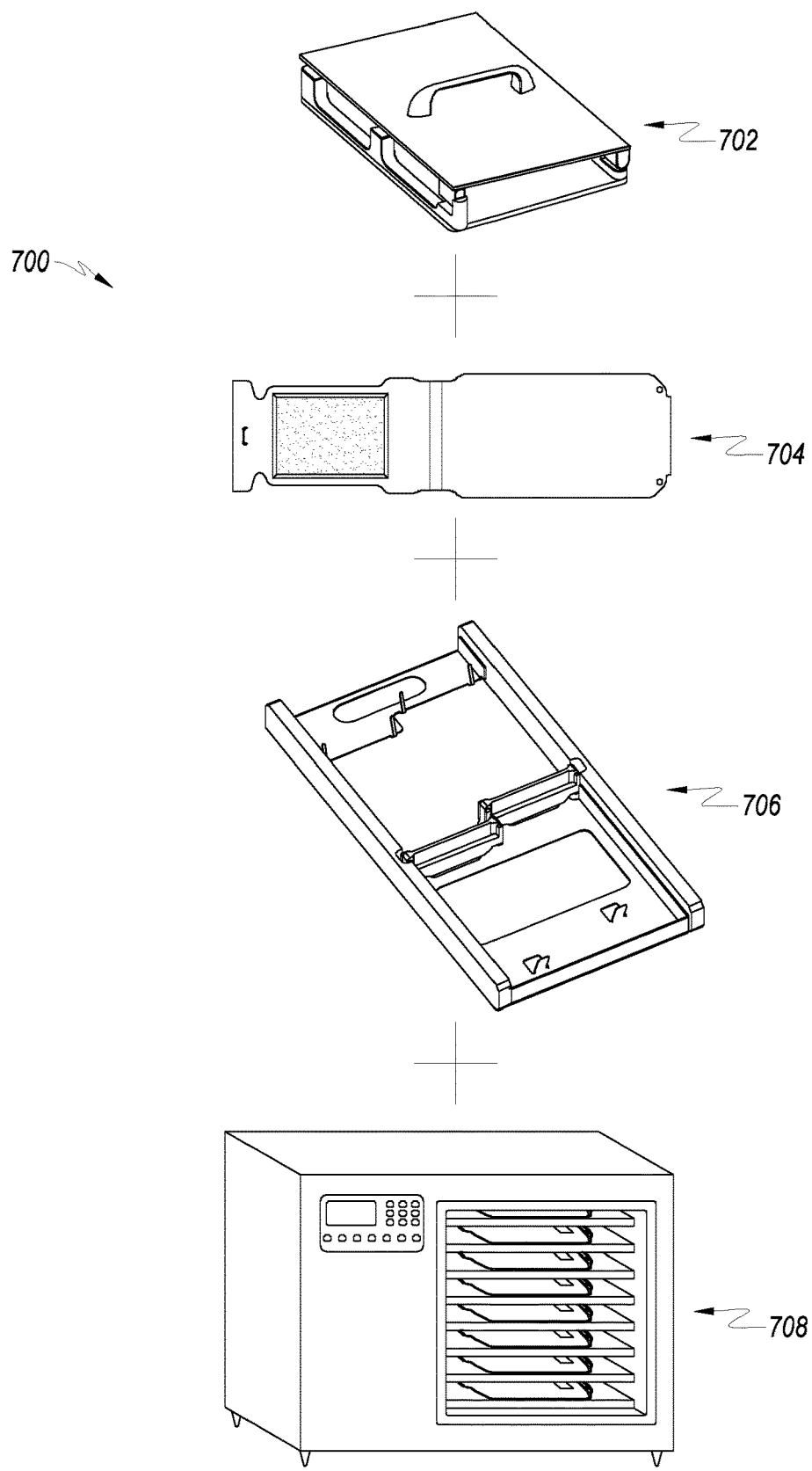
FIG. 7 is an illustration of a system for lyophilizing a fluid according to an embodiment of the present application.

As shown in FIG. 1, the lyophilization container 100 is comprised of two principal sections: non-breathable section 102 and breathable section 106, joined at peelable region 120. In a native or initial state, the internal cavities of non-breathable section 102 and breathable section 106 are isolated from one another by a temporary peelable seal in peelable region 120. In a non-native or open state, the temporary peelable seal of peelable region 120 has been removed and the internal cavities of non-breathable section 102 and breathable section 106 are in fluid communication with one another. Port region 104 defines an area within non-breathable section 102 that is configured to incorporate one or more fluidic ports. HOD 108 is a semi-rigid fixture which facilitates vapor flow in the container, and which is held in place by HOD capture zones 110. Tear away tail 122 is a container region configured to be torn away from breathable section 106 and which includes a hanger hole for hanging. Handle recesses 116 are configured to cooperate with optional system components such as a fill fixture (as shown in FIG. 7). Breathable membrane 112 is incorporated into breathable section 106 by inner membrane weld 114, which is a hermetic seal. Outer perimeter weld 118 is also a hermetic seal and defines the outer perimeter of the non-breathable section 102 and the breathable section 106, including the port region 104.

The overall length of the lyophilization container 100, denoted as "L" is approximately 50 cm. In embodiments, overall length may be any dimension suitable for placement of the container in a shelf lyophilizer or other lyophilizer, any dimension suitable for increasing or decreasing vapor flow resistance, or any dimension suitable for increasing or decreasing the thickness of the frozen liquid, such as between 30 cm and 70 cm, or more preferably between 40 cm and 60 cm.

In the example shown, the length of non-breathable section 102, measured from the midpoint of the peelable region, is approximately 28 cm. In embodiments, the length of non-breathable section 102 may be any suitable dimension, such as between 20 cm and 40 cm, or more preferably, between 24 cm and 32 cm. The length of breathable section 106, measured from the midpoint of the peelable region and including tear away tail 122, is approximately 22 cm. In embodiments, the length of breathable section 106 may be any suitable dimension, such as between 10 cm and 30 cm, or more preferably, between 18 cm and 26 cm.

In the embodiment shown, the widest portion of the container, denoted as "$W_{MAX}$," is approximately 14 cm and exists in the non-breathable section 102. In embodiments, $W_{MAX}$ may be any suitable dimension, such as between 10 cm and 20 cm, or more preferably, between 13 cm and 17 cm. In the embodiment shown, the narrowest portion of the container, denoted as "$W_{MIN}$," is approximately 7 cm and exists in handle recesses 116. In embodiments, $W_{MIN}$ may be any suitable dimension, such as between 5 cm and 12 cm, or more preferably, between 6 cm and 10 cm. The exemplary container dimensions of 14 cm by 50 cm described above are suited to lyophilize approximately 200 ml-300 ml of liquid plasma. The lyophilization of larger or smaller volumes would suggest different preferred dimensions.

The "top" or "front" of the lyophilization container 100 shown is essentially identical to the "bottom" or "back" of the container 100. That is, each of the top and the bottom of the container includes non-breathable material of the non-breathable section and breathable membrane of the breathable section. In alternative embodiments, the breathable membrane comprises a continuous sheet including an isoclinal (i.e., hairpin) fold causing the breathable membrane to bridge a portion of the top or front surface and a portion of the bottom or back surface. In yet another alternative embodiment, the breathable section might comprise breathable membrane only on the top of the container or only on the bottom of the container. In operation, the lyophilization container 100 is typically placed on a lyophilizer shelf such that the bottom or back of the container faces the lyophilizer shelf That is, during lyophilization, a portion of each of the non-breathable section 102 and the breathable section 106, including breathable membrane, face the lyophilizer shelf. Non-breathable section 102 should be in sufficient direct or indirect thermal communication with the lyophilizer shelf to facilitate conductive and/or radiative heat transfer. In yet further embodiments, only the non-breathable section might be in contact with the shelf and the breathable section might reside off the shelf. In certain other embodiments, the lyophilization container may be disposed vertically within a lyophilization chamber.

In operation, lyophilization container 100 exchanges fluids via ports positioned in the port region 104 of non-breathable section 102. Fluid exchanges occur only during initial filling of the container with liquid plasma and during the post-lyophilization filling of the container with sterile water for reconstitution and transfusion into a patient. Both prior to, and after, the sublimation of the frozen fluid and removal of vapor during lyophilization, non-breathable section 102 and breathable section 106 are isolated from one another. Prior to sublimation, non-breathable section 102 and breathable section 106 are isolated from one another by the temporary occlusion formed by a peelable seal in peelable region 120. After sublimation, a clamp is used to create the occlusion of the container in the peelable region 120 encompassing the transition between the non-breathable section 102 and breathable section 106. In this respect, the position of the occlusion in the peelable region 120 defines the boundary between non-breathable section 102 and breathable section 106.

Outer perimeter weld 118 defines the outer perimeter of the container, except tear away tail 122 in certain embodiments, and includes port region 104 of the non-breathable section 102. Outer perimeter weld 118 has an average width of approximately 7 mm. In embodiments; however, outer perimeter weld 118 may be any suitable width, such as between 2 mm and 12 mm, and may further be variable by up 3 mm along its length.

Inner membrane weld 114 surrounds the breathable membrane 112 within breathable section 106. Inner membrane weld 114 also has average width of approximately 7 mm; however, in embodiments, inner membrane weld 114 may be any suitable width, such as between 2 mm and 12 mm, variable by up 3 mm along its length.

Port region 104 is the portion of the outer perimeter weld 118 of non-breathable section 102 configured to incorporate one or more fluidic ports capable of forming a sterile fluid pathway between the lyophilization container and any of several other fluid containers. Port region 104 is also configured to facilitate transfusion to a patient.

In addition to encompassing the boundary between non-breathable section 102 and breathable section 106, peelable region 120 is adapted to facilitate the evolution of the container throughout its life cycle. Occlusion of the container 100 in the peelable region 120, either initially by the intact peelable seal, or by subsequent occlusion (e.g., clamping), creates a temporary impermeable or substantially impermeable seal, eliminating fluid communication between the non-breathable section 102 and breathable section 106. That is, in operation, an initial occlusion created by an intact peelable seal isolates non-breathable section 102 from the breathable section 106 prior to the introduction of fluid via ports in port region 104. Upon formation of a frozen ice structure (i.e., a frozen fluid structure to be lyophilized) a pressure differential is generated by the application of vacuum in the lyophilization chamber resulting in an opening of the temporary peelable seal. In this unoccluded state, the container includes a generous, open pathway for vapor flow between the non-breathable section 102 and breathable section 106. Prior to opening the lyophilization chamber, the container is again occluded (e.g., by a clamp) in the peelable region 120. The ability of the container to continually evolve in form and function ensures that no contact occurs between the subject fluid and the breathable section 106 by causing the subject liquid to be isolated and frozen in only the non-breathable section 102 and allowing only the vapor flow from sublimation and desorption to contact the breathable section 106. That is, embodiments of the present application are configured to create a continuous physical separation between the subject fluid and the breathable section 106. Accordingly, the non-breathable section 102 is adapted to accommodate any of a solid, a liquid or a gas, whereas the breathable section 106 is adapted to accommodate only a gas (i.e., a gas only section).

Peelable region 120 is approximately 1 cm in width; however, in embodiments, the peelable region 120 may be between 0.5 cm and 3.0 cm wide, such as between 0.8 cm and 1.5 cm wide. The nearest edge of the peelable region 120 is preferably positioned within 5 cm of the breathable membrane 112 of the breathable section 106 but may be positioned between 0.2 cm and 10 cm, such as between 3 cm and 7 cm, from the breathable membrane 112. The peelable region 120 should be sufficiently proximate to the breathable membrane 112 to ensure the efficient use of container materials and to minimize the distance that vapor must flow to exit the container, yet sufficiently distant from the breathable membrane 112 to allow for the creation of a permanent seam in non-breathable material between the occlusion and the breathable membrane post lyophilization. The creation of a permanent seam in non-breathable material between the occlusion and the breathable membrane material post-lyophilization creates a permanent seal, allowing for a permanent separation of container sections and the removal and disposal of the breathable section 106. Removal of the breathable section 106 is a further step in the evolution of the container. Removal of the breathable section 106 minimizes the volume and the mass of the final product, which is desirable for both transportation and storage. Additionally, removal of breathable section 106 transforms non-breathable section 102 into a more traditional container suitable for fluid transfusion into a patient. In embodiments, tear away tail 122 may optionally be removed from breathable section 106 and may further optionally be attached to non-breathable section 102 in order to create a means by which the final container can be hung by an operator. The subsequent attachment of the tear away tail 122 to the breathable section 102 may be performed using any suitable equipment, including the heat-sealing equipment used to create the permanent seam created to contain the final product in the non-breathable section 102.

In embodiments, the initial presence of an intact peelable seal in the peelable region 120 may provide a visual indicator demarcating the position of the peelable region 120. However, embodiments may include one or more additional position indicators. For example, the peelable region 120 may further be indicated by lines, by a color scheme, or by any other conventional means of visual indication. In embodiments, a choice of material or texture may further indicate the position of the peelable region 120. For example, a bumped, an etched, or any other type of surface texture or treatment may provide an indication of the position and boundaries of the peelable region 120. In embodiments, any of such position indicators, materials, textures or the like may also be chosen for one, or both, of the inner or outer surfaces of container material in the peelable region 120 to impart improved sealing characteristics (e.g., smooth materials), to impart an improved ability of the materials to pull apart from one another, or to pull apart from ice formed during freezing of the subject fluid (e.g., textured materials). In embodiments, an opened peel seal may expose or result in smooth surfaces in a peelable region which may be a favorable condition for a subsequent occlusion by a clamp. Material and design choices for the peelable region 120 should consider that the initial intact peelable seal and the subsequent occlusion created in the peelable region 120 must reliably form a temporary impermeable seal. However, it should be noted that in some circumstances, an occlusion may not be a perfectly impervious or hermetic barrier or seal. That is, in certain situations, minor or insubstantial leakage across an occlusion may be acceptable.

As noted, the initial occlusion of the container in the peelable region 120 is provided by an intact peelable seal. Subsequent occlusion in the peelable region 120 occurs by other means, such as by manual clamping or by various automated or semi-automated means. Exemplary manual clamps may include, but are not limited to, screw clamps or bag clips that are in common usage. Further exemplary clamps may include specialized clamps, such as a two-piece guillotine clamp. Various automated or semi-automated occlusion means may, for example, include mechanical compression means incorporated into or actuated by the shelves of, or the shelf system of, a lyophilizer. Such means of occlusion may operate in conjunction with a lyophilization loading tray or tray assembly, such as that shown in FIG. 7.

In the embodiment shown in FIG. 1, the non-breathable material is ethylene-vinyl acetate (EVA). EVA exhibits several advantageous properties including its relative strength, its relative elasticity and resilience at low temperatures, its relative crack resistance and the ease with which it may be manufactured. EVA also exhibits comparatively favorable thermal transfer properties. Nonetheless, in embodiments, material choices for non-breathable material are not limited, and may include a variety of non-breathable materials that exhibit preferable characteristics, such as thermoplastic elastomers (TPEs). TPEs are relatively soft and flexible, and exhibit advantages for several healthcare applications. For instance, TPEs can be sterilized using autoclaves, gamma irradiation, or ethylene oxide. Further, TPEs can be designed to be biocompatible, to have high purity, and to have low levels of extractable and leachable substances. TPEs are also recyclable and are a comparatively favorable material for cryogenic storage.

Linear, low density polyethylene (LLDPE) may also be desirable for use as non-breathable material. LLDPE is preferable to certain other materials due to its favorable puncture and impact resistance and to its high tensile strength. For instance, as compared to LDPE, LLDPE exhibits superior flexibility and resistance to cracking, thus making it more suitable for certain thin film applications.

Materials selected for non-breathable material must maintain strength at low temperatures (e.g., −30° C. to −60° C.) as is required for lyophilization. Certain materials exhibiting a low surface energy and super-hydrophobicity may further be incorporated into the interior surface of the non-breathable section to facilitate an improved release of the ice structure from the inner surfaces of the container after freezing and before drying.

In embodiments, various additional or alternative plastic films may be incorporated into non-breathable section 102, or to all areas of the container with non-breathable material for a particular purpose or application. For example, materials may be implemented for any of improved impermeability, improved heat-sealing characteristics or improved mechanical strength. In yet further embodiments, various additional features may also be included in non-breathable section 102. For instance, a section of relatively clear container material may be incorporated into non-breathable section 102 to allow visual inspection of the subject fluid before, during or after lyophilization.

Notably, an initial intact peelable seal may require specific material and design choices to function optimally under lyophilization conditions. In a preferred embodiment, the peel seal is constructed using dissimilar top and bottom materials. Dissimilar top and bottom materials may more easily and reliably peel away from one another under vacuum. In embodiments using the same or similar top and bottom materials, an additive (e.g., a slip agent) may be applied to one of the materials in order to achieve improved peeling characteristics under vacuum. In another preferred embodiment, the seal may further include materials having dissimilar textures. For instance, the top material of a peelable seal may comprise a bumped or etched texture, and the bottom material may comprise a smooth texture, or vice versa. In embodiments, dissimilar materials and dissimilar textures may be implemented simultaneously.

In embodiments, specific manufacturing parameters may further be required to generate a desirable peelable seal. Preferably, a peelable seal is 0.95 cm in width (+/−0.076 cm); however, the width of the peelable seal may vary depending upon various factors, such as the type of fluid to be lyophilized, choice of container materials, etc. In embodiments, the manufacture of a peel seal using a heat seal machine may require the heating elements (i.e., heat bars) of the heat sealer to be applied to the container materials within a particular range of temperature, pressure and duration. In a preferred embodiment, heating elements are maintained at a temperature of approximately 64° C. (+/−0.25° C.) and applied to container materials at a pressure of approximately 50 psi for 40 seconds. In further embodiments, however, these parameters are not limited and may vary according to a particular application. For instance, heating element temperature may be between 60° C. and 70° C., such as between 63° C. and 67° C. Likewise, clamping pressure may be between 30 psi and 80 psi, such as between 40 psi and 70 psi. Similarly, clamping duration may occur over a time range of between 10 seconds and 90 seconds, such as between 40 seconds and 70 seconds.

Because impulse or discontinuous heat may result in cross linking of the material and a resultant malfunction, the temperature of the heating elements is preferably maintained continuously within a narrow range. To achieve a continuous heat source, embodiments of the heat seal machine may be specialized to include a relatively large amount of material capable of storing sufficient heat energy to recover quickly from the initial temperature drop caused by initial contact with the relatively cool container material, yet which does not overcompensate with a subsequent addition of excess heat. For example, a customized or specialized heat seal machine may be required, and which comprises one or more large metal components as part of its clamping or sealing mechanism. In embodiments, the metal component(s) may be heated using various conventional means such as an electrical strip or a liquid source such as water, glycol, or other substance capable of storing sufficient energy. In further embodiments, indirect means such as infrared or RF may be applied to heat the metal component(s). Alternative indirect means for creating the peelable seal in the absence of the metal component(s) may include ultrasonic welding and laser applications.

In embodiments, the above-described combination of material choices and manufacturing parameters are preferred for a seal measuring 0.95 cm in width (+/−0.076 cm) and may result in a peelable seal which opens reliably and evenly across its length under lyophilization conditions (e.g., at lyophilization chamber pressures of between 400 Torr and 100 Torr and lyophilization chamber temperatures of between −30° C. and −60° C.).

Figure 2:
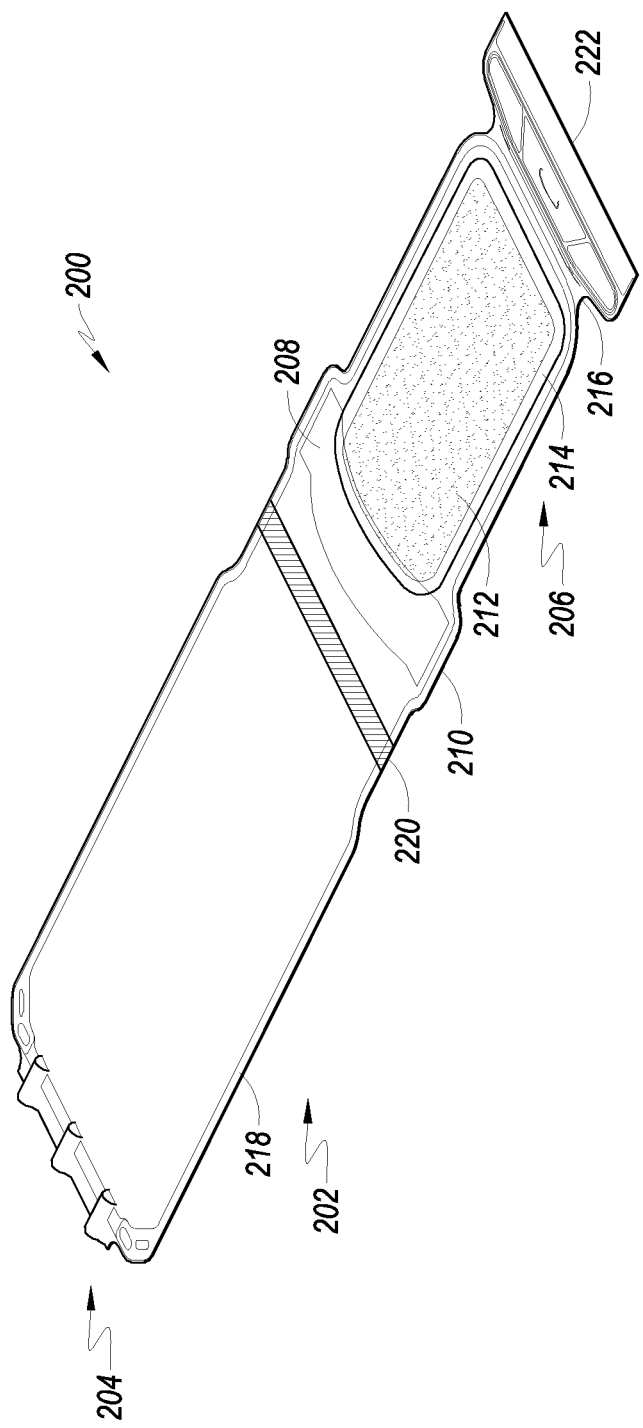
FIG. 2 is a perspective view of the lyophilization container of FIG. 1.

FIG. 2 is a perspective view of the lyophilization container of FIG. 1.

Referring to FIG. 2, the lyophilization container 200 includes a non-breathable section 202, including a port region 204; a breathable section 206, including a Hold Open Device (HOD) 208, HOD capture zones 210, a breathable membrane 212, an inner membrane weld 214 and handle recesses 216; an outer perimeter weld 218; a peelable region 220 and a tear-away tail 222.

Although FIG. 1 and FIG. 2 depict an irregularly shaped container, further embodiments may comprise a more regular geometry, such as an essentially rectangular shape. Additional container configurations may also include alternative irregularities, e.g., the dimensions or geometry of a particular region or feature may be altered to achieve design or performance objectives. A variety of container modifications may be understood by one of skill in the art to be within the scope and spirit of this application.

FIG. 3A is a plan view of a non-breathable section of a lyophilization container according to an embodiment of the present application.

Referring to FIG. 3A, non-breathable section 300 comprises a non-breathable material 302; and an outer perimeter weld 304, including a port region 306 incorporating fluidic ports 308; and a portion of a peelable region 310.

Non-breathable section 300 is comprised of the non-breathable material described above. The boundaries of non-breathable section 300 include outer perimeter weld 304, including port region 306, and the midpoint (i.e., the estimated position of an occlusion) of the peelable region 310. That is, when the container is occluded in the peelable region 310, non-breathable section 300 may be defined as the section of the container on the side of the occlusion that is non-breathable. When an occlusion is not present in the peelable region 310, the boundary of the non-breathable section may be approximated as the midpoint of the peelable region 310, as shown in FIG. 3A.

FIG. 3B is an expanded view of the port region of the non-breathable section of the lyophilization container of FIG. 3A.

Referring to FIG. 3B, port region 306 includes three ports 308. The ports 308 define the manner in which the lyophilization container exchanges fluids with other vessels and containers. The ports 308 must accordingly provide secure, sterile connections which eliminate the potential for breakage, contamination or misconnection, and must function across every phase of use including filling, lyophilization, storage, reconstitution and, in the case of lyophilized plasma, infusion. In embodiments, the configuration and number of ports 308 may vary depending on a particular application. For instance, embodiments may include between 1-5 ports, such as 3 ports. Ports 308 may further include connections which are either resealable or non-resealable.

Ports 308 shown in FIG. 3B may be adapted to include a variety of ports. For example, ports 308 may include any of a spike port, a docking port and a reconstitution port. A spike port may be included to facilitate reinfusion of a reconstituted blood product into a patient. An exemplary spike port may be any weldable spike port known in the art which is compatible for use in lyophilization containers. Examples of suitable materials for use in spike port include polyvinyl chloride (PVC) and ethylene-vinyl acetate (EVA) (e.g., such as is manufactured by Carmo of Denmark). In other embodiments, a polypropylene (PP) spike port may be desirable.

A docking port may be included to connect the lyophilization container with another fluid container, such as a blood pooling container or pooling container set. A docking port may further be used to introduce air o+r other gas into the lyophilization container. Air or other gas may, for example, be introduced to create a vapor space above the subject liquid or to regulate pH. An exemplary docking port comprises PVC tubing. In embodiments, however, dock port may include any suitable docking fixtures or tubing which are known in the art.

A reconstitution port may be included to accept an inflow of reconstitution fluid into the lyophilization container. An exemplary reconstitution port 308 may include a male or a female Luer-Lock type connection in order to prevent accidental misconnection. One example of such a connection is the Correct Connect® system that is a standardized connection system used in apheresis applications. In embodiments, various one-way valves and other means for providing an error proof connection may also be adapted for use with the reconstitution port 308. Notably, the type of connection used for reconstitution is particularly important. That is, the handling of reconstitution fluids entails the potential risk of a direct transfusion of the reconstitution fluid into the patient. Such an event constitutes a serious and immediate health hazard. For this reason, it is important that the reconstitution port and related connections be highly conspicuous and be incompatible with the other ports in order to avoid an occurrence of accidental misconnection.

Figure 4:
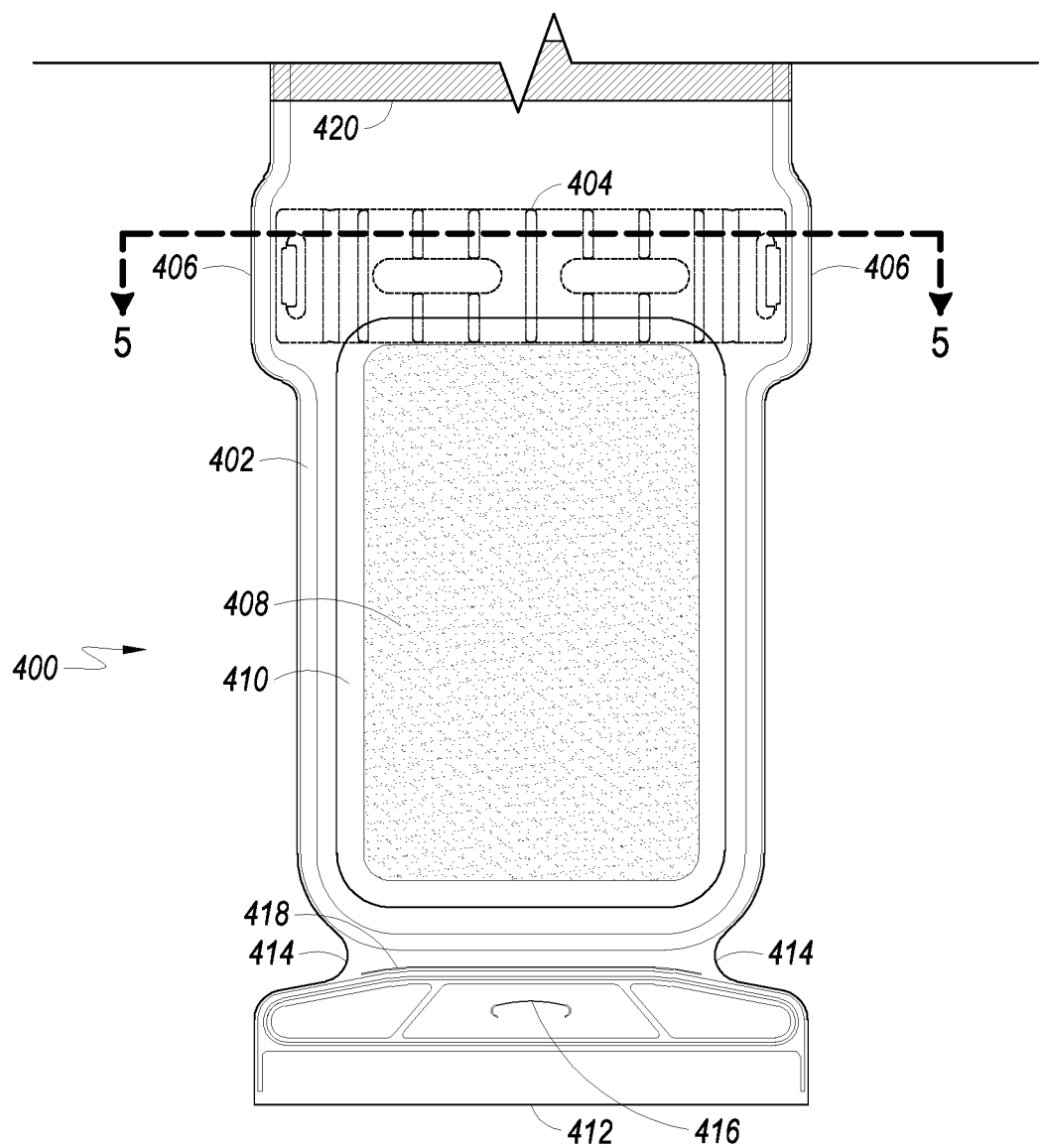
FIG. 4 is a plan view of a breathable section of a lyophilization container according to an embodiment of the present application.

FIG. 4 is a plan view of a breathable section of a lyophilization container according to an embodiment of the present application.

Referring to FIG. 4, breathable section 400 comprises an outer perimeter weld 402; a Hold Open Device (HOD) 404; HOD capture zones 406; a breathable membrane 408; an inner membrane weld 410; a tear away tail 412; handle recesses 414; a hanger hole 416; a tear seam 418; and a portion of a peelable region 420.

The midpoint (i.e., estimated position of occlusion) of the peelable region 420 constitutes a boundary of breathable section 400. That is, when the container is partitioned in the peelable region 420 by either an intact peelable seal or by a subsequent occlusion, breathable section 400 may be defined as the section of the container on the side of the occlusion that is breathable. When an occlusion is not present in the peelable region 420, the boundary of the breathable section 400 may be approximated as the midpoint of the peelable region, as shown in FIG. 4. Notably, although tear away tail 412 is not itself breathable, it may be considered part of breathable section 400 for convenience and for its attachment thereto.

Breathable section 400 comprises breathable membrane 408 embedded within non-breathable material. Inner membrane weld 410 is a sterile seal defining the boundary between the breathable membrane and non-breathable material. Outer perimeter weld 402 is a sterile seal defining the outer perimeter of breathable section 400.

In certain embodiments, breathable membrane 408 may comprise only one material. In other embodiments, breathable membrane 408 may comprise two or more materials, for example, breathable membrane may comprise a membrane laminate consisting of a breathable membrane and a backing material. In embodiments comprising a laminate, membrane material may include p (PTFE) or expanded p (ePTFE). ePTFE membranes are preferable to other membranes for several reasons. For instance, ePTFE provides a microstructure that may be precisely controlled, which results in the ability to obtain a desired a pore size distribution. Further, ePTFE is essentially inert, is operable across a large temperature range and can withstand harsh environments. The hydrophobicity of these materials also ensures that no liquid will escape the container in the event of a prematurely opened peel seal. For at least these reasons, ePTFE provides characteristics which are preferable in comparison to other materials.

An ideal pore size for an ePTFE membrane may be between 0.1 micron (µm) to 0.5 µm, such as 0.15 µm to 0.45 µm, or 0.2 µm to 0.3 µm. An ePTFE membrane having pore sizes in this range exhibits relatively efficient vapor transmission characteristics while maintaining a sterile barrier capable of eliminating the ingress of contaminants.

A reinforcing or backing material is designed to bond breathable material to non-breathable material without impairing the functionality of the breathable membrane 406. The addition of a reinforcing or backing material improves the structural integrity of the container. That is, the reinforcing material must bond with the breathable membrane, must bond with the non-breathable material, and must have a pore size that does not impede vapor transmission across the breathable membrane during lyophilization. Exemplary reinforcing materials are preferably a 50:50 polypropylene/polyethylene blend. In embodiments, however, preferable blend ratios may vary and may be between 40:60 and 60:40 polypropylene:polyethylene. Such backing materials are advantageous, inter alia, for their transition glass temperatures which are low enough to avoid material degradation during freezing at lyophilization temperatures, such as approximately −40° C.

In embodiments comprising a laminate, various additional or alternative plastic films may be incorporated into the breathable membrane or to the backing material to impart desired characteristics, such as favorable heat-sealing characteristics, improved permeability, or for overall mechanical strength.

HOD 404 is a semi-rigid, flat-sided elliptical fixture, captured within the breathable section 400 by HOD capture zones 406. HOD 404 is in an open mode in its native state, disposed circumferentially within the container cavity to facilitate a pathway for vapor flow between non-breathable section and breathable section 400. HOD 404 is positioned entirely within the breathable section 404, bridging portions of breathable membrane 408 and non-breathable material. Notably, in embodiments, HOD 404 shape is not limited, and various alternative HOD 404 designs may be implemented, such as a modified rectangle or other shape capable of facilitating vapor flow between container sections.

In various embodiments, HOD 404 may be a rigid or a semi-rigid fixture captured within, or fastened to the outside of, the breathable section 400 of the lyophilization container. The exact position of the HOD 404 may vary. For example, the HOD 404 may be positioned entirely within the non-breathable section, or within a region of non-breathable material of the breathable section. Alternatively, HOD 404 may extend into portions of both non-breathable material and breathable material. In yet further embodiments, HOD 404 may be positioned and configured to assist in the creation of the temporary seal between container sections. Preferably, HOD 404 is positioned proximate to the peelable region to minimize the distance between the HOD 404 and the placement of an occlusion in the peelable region 420. In the example shown, the nearest edge of HOD 404 is positioned approximately 2.5 cm from nearest edge of the peelable region 420. Nonetheless, HOD 404 placement may be further optimized according to a particular container configuration or peelable region 420 configuration.

HOD capture zone 406 is a portion of container material which protrudes in the width direction of the container and which serves as a pocket or cavity space in which HOD 404 is securely captured. In embodiments, aspects of the HOD capture zone 406 may be optimized. For instance, HOD capture zone 406 width or depth may vary according to a particular container configuration or HOD 404 configuration. In embodiments, HOD capture zone 406 width may be as much as 20 percent greater than the width of the HOD 404. Similarly, HOD capture zone 406 depth may be between 1 mm and 6 mm, such as between 2 mm and 4 mm. In yet further embodiments, the shape of HOD capture zone 406 may vary. For example, certain embodiments may include squared aspects or convex aspects, and so on. Those of skill in the art will appreciate that various optimizations to the size and shape of HOD capture zone 406 are within the scope and spirit of this application.

Tear away tail 412 is a multi-function region of breathable section 400 configured to contribute to the evolution of the container throughout its lifecycle. As shown, tear away tail 412 comprises a hanger hole 416 for hanging the container. Tear away tail 412 further forms a portion of handle recesses 414. Handle recesses 414 may cooperate with features of certain system components such as a gas fill fixture shown in FIG. 7. For example, in embodiments handle recesses 414 may cooperate with a fill fixture handle in order to secure the breathable section of the container to the fill fixture during a gas fill procedure for the purpose of eliminating clutter and to simplify the obtaining of system measurements. Tear seam 418 allows an operator to manually remove tear away tail 412 for disposal or for final attachment to non-breathable section. That is, tear away tail 412 may ultimately be attached to the final container of product (i.e., the non-breathable section) using conventional means, such as a heat-sealing machine used to make a permanent seam in the container.

Figure 5:
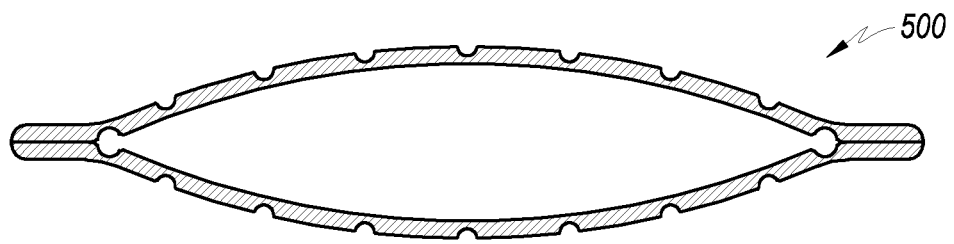
FIG. 5 is a section view of the Hold Open Device (HOD) of the embodiment shown in FIG. 4.

FIG. 5 is a section view of the Hold Open Device (HOD) of the embodiment shown in FIG. 4.

Referring to FIG. 5, HOD 500 is a semi-rigid fixture having an essentially ovular or elliptic shape incorporating pointed ends and flat sides. In the embodiment shown, HOD 500 is captured within the breathable section proximate to the peelable region. In other embodiments, the HOD 500 may be coupled to the outside of the container. Although generally the HOD 500 is designed to reside in, or on the outside of, the breathable section of the container, physically separated from the subject liquid throughout the container life cycle, various further embodiments could include HOD 500 in the non-breathable section.

Incorporation of the elliptic HOD 500 aids in the creation of a generous open region above a thin, uniform structure of ice. Preferably, the thin, uniform ice structure has a thickness of from 6 mm to 13 mm, such as 10 mm, to maximize the efficacy and efficiency of the container. Incorporating the HOD 500 assists in securing a generous vapor pathway between the non-breathable section and the breathable section and reduces overall vapor pressure in the container during sublimation. HOD 500 may also compliment the removal and/or creation of an occlusion in the peelable region. For example, HOD 500 may impart a tautness to container material which improves the reliability or quality of an occlusion. HOD 500 may likewise assist in the pulling apart of peelable region surfaces during a removal of the occlusion, thereby facilitating a re-creation of the vapor pathway between container sections. The pulling apart of peelable region surfaces can be complicated by the existence of ice formed on, or directly adjacent to, the occlusion as a result of an inadvertent wetting of peelable region materials by the subject fluid prior to the freezing step. Such wetting may be caused during the filling step, or by movement of the container. In this respect, HOD may compliment other means employed to address problems associated with the pulling apart of peelable region surfaces described herein, including material and related texture choices.

In the embodiment shown, HOD 500 comprises a semi-rigid high-density polyethylene (HDPE). In embodiments, however, several other rigid or semi-rigid materials may be implemented. For example, silicone, polypropylene, polyethylene, polyvinyl chloride (PVC) or certain other synthetic plastic polymers may be preferable HOD 500 material. In certain embodiments, semi-rigid materials may be incorporated for their ability to flex in response to an occlusion of the peelable region. In such embodiments, HOD may compress to some degree upon occlusion of the peelable region and may rebound toward an original shape upon removal of the occlusion. Such shape-memory behavior may assist in the maintaining of an open region above the subject liquid or ice and in the creation of generous vapor pathway between container sections. This may be especially pronounced in embodiments combining a semi-rigid HOD with other flexible container materials.

The external height of HOD 500 shown in FIG. 5 is 2 cm; however, in embodiments, external height may vary from 1.0 cm to 4 cm. The internal height is approximately 1.8 cm; however, in embodiments, the internal height may vary between 1 cm to 3 cm depending on the exact configuration and size of HOD. HOD width is the approximate width of the lyophilization container. HOD 500 depth is approximately 3.0 cm; however, in embodiments HOD depth may be between 0.5 cm and 5 cm. The overall size and shape of HOD 500 is not limited, and accordingly may vary depending on the desired configuration of a particular embodiment.

Figure 6:
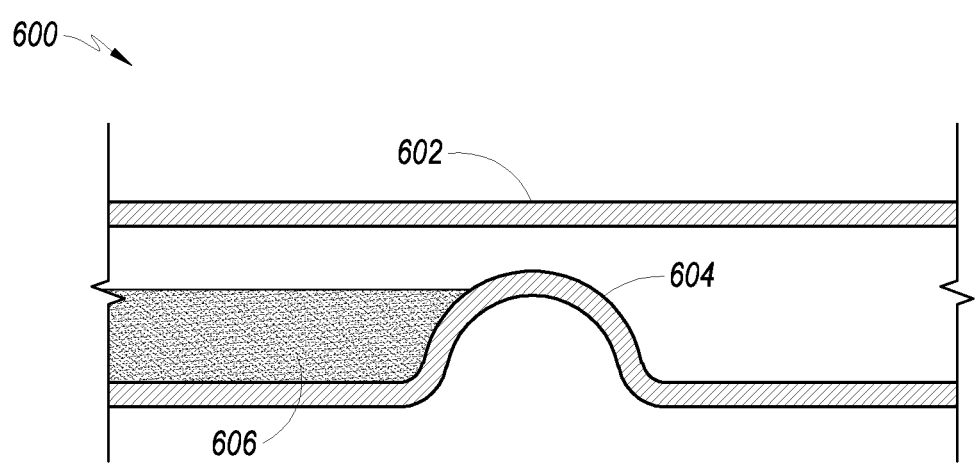
FIG. 6 is a side section view of an alternative configuration of a peelable region according to an embodiment of the present application.

FIG. 6 is a side section view of an alternative configuration of a peelable region according to an embodiment of the present application.

Referring to FIG. 6, peelable region 600 includes top material 602; dam 604; and a liquid 606.

In the embodiment shown in FIG. 6, peelable region 600 is incorporated into a lyophilization container disposed horizontally on a lyophilizer shelf. Top material 602 of peelable region 600 comprises non-breathable material and is positioned opposite the container cavity from dam 604. Dam 604 is a rigid or semi-rigid container feature capable of maintaining a segregation of the liquid 606 input to the non-breathable section. Dam 604 height measured from the shelf of the lyophilizer can be any height which exceeds the height of liquid input into non-breathable section. In this respect, dam 604 prohibits the flow of fluid from non-breathable section into breathable section, as shown in FIG. 6.

Dam 604 shown in FIG. 6 comprises a dome shape; however, in embodiments, other dam designs may be desirable. For instance, dam designs including a flat top, or dam designs configured to cooperate with a particular occlusion device or member may be desirable. Preferred dam 604 materials include materials capable of forming a peelable seal with top material 602, including but not limited to textured materials and materials including an additive. In a preferred embodiment, dam 604 material is dissimilar to top material 602; however, in certain embodiments, dam material may be the same as top material. In yet further embodiments, dam features may be incorporated into a lyophilization container designed to hang vertically. In embodiments, dam features may be included on one or both sides of a peelable region to maintain a segregation of the fluid input into the non-breathable section.

FIG. 7 is an illustration of a system for lyophilizing a fluid according to an embodiment of the present application.

Referring to FIG. 7, the system 700 includes a gas fill fixture 702; a lyophilization container 704; a lyophilization loading tray 706; and a lyophilizer 708.

The lyophilization container 704 is a container as described in embodiments of this application. That is, container 704 is a flexible, multi-part container including a peelable seal in a peelable region.

System 700 may vary in embodiments. For example, system 700 embodiments may exclude the gas fill fixture 702 or the lyophilization loading tray 706 altogether. In further embodiments, system 700 may employ components which are differently configured than those shown. For instance, lyophilizer 708 may be used in conjunction with a freezer that is a separate system component. As can be readily envisioned by one of skill in the art, various further modifications to the system or its individual components may be made based on, e.g., a particular container configuration, or the like, and are accordingly within the scope and spirit of this application.

As noted, embodiments of the lyophilization container(s) described herein are configured to continually evolve as the lyophilization process moves through its cycle. Described below are exemplary workflows which illustrate and facilitate container evolution.

Figure 8:
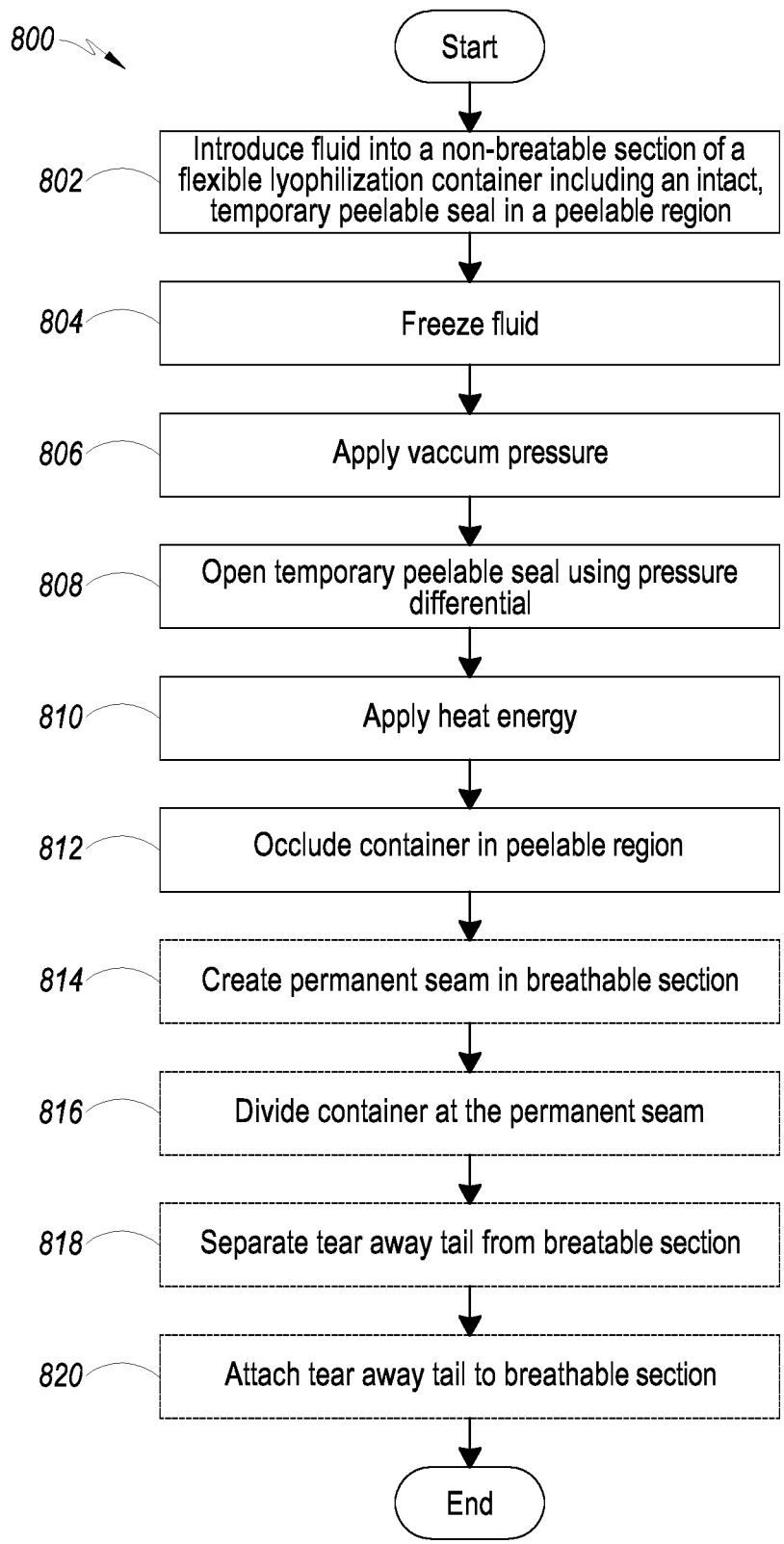
FIG. 8 is a workflow schematic illustrating a lyophilization process according to an embodiment of the present application.

FIG. 8 is a workflow schematic illustrating a lyophilization process according to an embodiment of the present application.

Referring to FIG. 8, in step 802, a subject fluid (e.g., blood plasma) is introduced into the non-breathable section of a container including an intact, temporary peelable seal in a peelable region of the container. In step 804, the fluid is frozen, creating a thin, uniformly thick structure of ice in the non-breathable section. In step 806, vacuum pressure is applied. In step 808, the peelable seal is opened once a sufficient pressure differential exists between the lyophilization chamber and the cavity of the non-breathable container section. Opening of the peelable seal creates a communication pathway between container sections. In step 810, heat energy is applied. The combined application of vacuum pressure and heat energy facilitates sublimation and desorption, causing a phase change in the ice structure from the solid phase directly to the vapor phase. Vapor released from the ice structure then flows through the container cavity via the unoccluded peelable region and escapes through the breathable section, leaving the lyophilized plasma cake (i.e., the ice structure now dehydrated as a result of lyophilization) in the non-breathable section. In step 812, the container is occluded in the peelable region to prevent contamination of the lyophilizate. In step 814, a permanent seam is optionally created in the non-breathable material of the breathable section between the occlusion and the HOD. In step 816, the container is optionally divided at the permanent seam and the breathable section is discarded, leaving the lyophilized end-product in the non-breathable section. In step 818, the tear away tail is optionally separated from the breathable section. In step 820, the tear away tail is optionally attached to the non-breathable section.

Referring to step 802, the introduction of fluid may be referred to as pre-loading. During preloading, between 250 ml to 500 ml of fluid (e.g., blood plasma) are inputted into the non-breathable section of the multi-part lyophilization container. The container is then placed horizontally on the shelf of a lyophilizer, "front" or "top" side upward facing.

Referring to step 804, the fluid is frozen to a temperature of approximately −40° C. In embodiments, however, initial freezing temperature may range from −30° C. to −60° C., such as between −40° C. to −50° C.

Referring to steps 806 to 810, the application of heat energy and vacuum pressure serves multiple functions. For instance, the application of vacuum lowers the pressure in the lyophilization chamber causing a pressure differential between the lyophilization chamber and the cavity within the non-breathable section of the lyophilization container. This pressure differential, in turn, results in an expansion of the non-breathable section of the container. Eventually, this expansion of the non-breathable section of the container causes a peeling apart of the peelable seal. In embodiments, the pressures required to achieve this phenomena may range from between 400 Torr and 100 Torr, such as between 250 Torr and 150 Torr. Once the peelable seal is sufficiently peeled away, the heat energy and vacuum pressure continue to facilitate sublimation and desorption. Notably, although heat energy is applied in step 810 after peeling of the peel seal in step 808, alternative embodiments may introduce heat energy along with the introduction of vacuum pressure. A preferable drying temperature is approximately −25° C.; however drying temperature may range from −20° C. to −60° C., such as between −20° C. to −40° C. Owing to the generous vapor pathway between container sections and the large surface area of breathable membrane in the breathable section, vapor from the ice structure escapes relatively freely from the container. This, in turn, results colder temperatures during lyophilization and therefore an improved quality of the final dry product. In addition, a diminution in sublimation times as compared to conventional lyophilization techniques is realized. Further, embodiments result in reduced vapor pressures in, and an increase in mass transfer across, the breathable section, which may result in a sufficient drying of the ice structure solely during a single drying phase. That is, embodiments may obviate the need for the secondary drying phase of traditional two-phase drying methods (i.e., desorption).

Referring to step 812, an occlusion is created in the peelable region of the container, creating a temporary seal between the breathable section and the non-breathable section. In embodiments, this occlusion is created using a clamp.

In optional step 814, a permanent seam is created in non-breathable material of the breathable section. The permanent seam isolates the lyophilized cake in the non-breathable section. In the schematic shown, permanent seam step 814 is a discreet step. That is, an ancillary piece of equipment is used to create the permanent seam or seal. In further examples, the creation of a permanent seam in step 814 may be integrated into step 812. In such embodiments, the occlusion means (e.g., a clamp) may incorporate the permanent sealing means.

In optional step 816, the dividing of the container and removal of the breathable section represents an evolution of the container into its most compact form. Removal of the breathable section eliminates the potential for moisture and oxygen ingress into the dried product, thereby increasing shelf life and plasma stability. Additionally, the reduced size of the final lyophilizate container is more convenient for each of transportation, storage, reconstitution and infusion.

In optional steps 818 and 820, respectively, the tear away tail is manually torn away from the breathable section at the tear seal and is attached to the non-breathable section. In embodiments, step 818 may be performed using the heat-sealing machine used to create the permanent seam in step 812.

Figure 9:
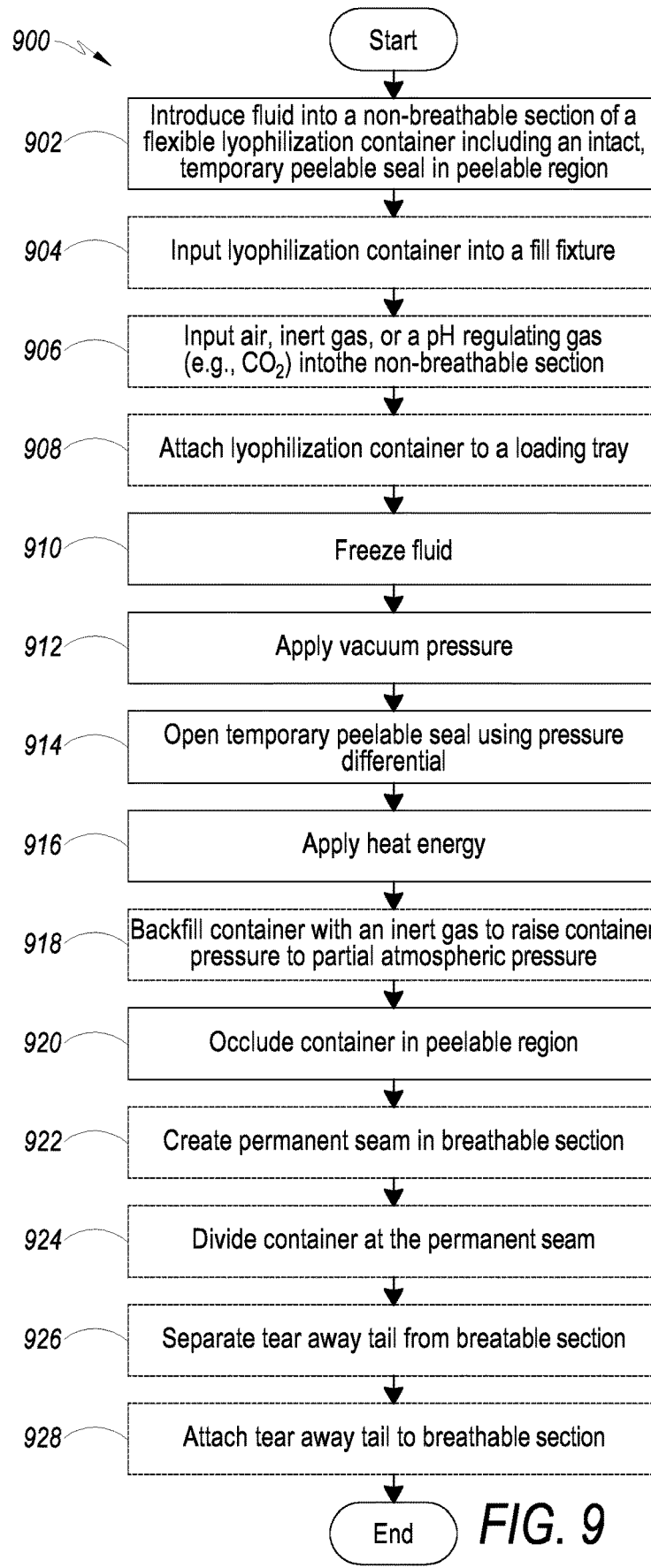
FIG. 9 is workflow schematic illustrating a lyophilization process according to another embodiment of the present application.

The workflow of FIG. 9 represents the workflow of FIG. 8 with the addition of various optional steps.

FIG. 9 is a workflow schematic illustrating a lyophilization process according to another embodiment of the present application.

Referring to FIG. 9, in step 902, a subject fluid (e.g., blood plasma) is introduced into a non-breathable section of a flexible lyophilization container including an intact peelable seal in a peelable region of the container. In step 904, the lyophilization container is optionally inputted into a fill fixture. In step 906, air, inert gas (e.g., nitrogen), or a pH regulating gas (e.g., $CO_2$) is optionally introduced into the non-breathable section through a port in the port region (e.g., a docking port). In step 908, the lyophilization container is optionally attached to a loading tray for optimizing container performance during lyophilization. In step 910, the liquid in the container is frozen, creating a thin, uniformly thick structure of ice in the non-breathable section. In step 912, vacuum pressure is applied. In step 914, the peelable seal is opened once a sufficient pressure differential exists between the lyophilization chamber and the cavity of the non-breathable container section. Opening of the peelable seal creates a communication pathway between container sections. In step 916, heat energy is applied. The combined application of vacuum pressure and heat energy facilitates sublimation and desorption, causing a phase change in the ice structure from the solid phase directly to the vapor phase. Vapor released from the ice structure then flows through the container cavity via the unoccluded peelable region and escapes through the breathable section, leaving the lyophilized plasma cake (i.e., the ice structure now dehydrated as a result of lyophilization) in the non-breathable section. In step 918, the container is optionally backfilled with an inert gas to raise container pressure to partial atmospheric pressure. In step 920, the container is occluded in the peelable region to prevent contamination of the lyophilizate. In step 922, a permanent seam is optionally created in the non-breathable material of the breathable section between the occlusion and the HOD. In step 924, the container is optionally divided at the permanent seam and the breathable section is discarded, leaving the lyophilized end-product in the non-breathable section. In step 926, the tear away tail is optionally separated from the breathable section. In step 928, the tear away tail is optionally attached to the non-breathable section.

Referring to optional step 904, a gas fill fixture is used to assist the operator in filling the lyophilization container with a gas. That is, the lyophilization container is inputted into a gas fill fixture and subsequently filled with a gas. The gas fill fixture provides an operator with an indication of a correct gas fill volume. In an exemplary embodiment, the gas fill fixture shown in FIG. 7 may be used. In alternative embodiments, the exact configuration of the gas fill fixture is not limited and may vary according to a number of variables including as container configuration, process parameters, etc.

In optional step 906, air (or nitrogen or another inert dry gas), or a pH regulating gas (e.g., $CO_2$) is introduced into the lyophilization container. Air can be introduced to create a generous physical separation, i.e., a vapor space, between the container material and the preloaded fluid. In exemplary embodiments, the introduction of a vapor space may cause container pressure to reach between 0.3 Pound per square inch (Psi) and 1.0 Psi, such as 0.5 Psi (approximately 26 mmHG). Advantageously, the creation of a vapor space in the container creates a generous free surface for sublimation to occur and may reduce the amount of ice "sticking" to the container material during and after the freezing step. A pH-regulating gas may be introduced to the lyophilization container to regulate pH. In an alternate embodiment, a pH-regulating gas may be introduced during step 914 described below.

Referring to optional step 908, a loading tray or loading tray assembly (as shown in FIG. 7) is used to optimize container performance. That is, the lyophilization container is attached to a loading tray or loading tray assembly and subsequently loaded into the lyophilizer. The loading tray or loading tray assembly includes features which optimize container performance. In an exemplary embodiment, the loading tray shown in FIG. 7 may be used. In alternative embodiments, the exact configuration of loading tray is not limited and may vary according to a number of variables including as container configuration, process parameters, etc.

In optional step 918, the lyophilization container is backfilled to partial atmospheric pressure with pH regulating gas (e.g., $CO_2$). In exemplary embodiments, backfill pressure is 120 Torr (or 120 mmHG) absolute pressure. In embodiments, backfill pressure may range from between 40 mmHG and 200 mmHG, such as between 100 mmHG and 140 mmHG. Once at partial atmospheric pressure, the container is occluded, and then permanently sealed in steps 918 and 920, respectively. Occlusion and/or sealing of the container while at a pressure lower than atmospheric pressure causes the container to collapse and reduce its volume when the container is exposed to atmospheric pressure. This process also secures the pH regulating gas in the non-breathable portion and prevents an ingress of oxygen and moisture into the container. Since the resultant container has been occluded and/or sealed at a pressure that is less than atmospheric pressure, and since final container volume will be in a reduced volume condition once the vacuum of the lyophilizer is removed, the final lyophilized product can be stored and transported more easily. Backfilling in this manner is particularly applicable to container embodiments having flexible materials or components since such a diminution of container volume would not be possible with a rigid, inflexible lyophilization container.

In optional step 922, a permanent seam is created in the non-breathable material of the breathable section between the occlusion and the HOD. In optional step 924, the container is divided at the permanent seam and the breathable section is discarded, leaving the lyophilized end-product in the non-breathable section. In optional step 926, the tear away tail is separated from the breathable section. In optional step 928, the tear away tail is attached to the non-breathable section.

In the workflows described above, the means for creating the occlusion are not limited. For example, the occlusion means may comprise a two-part clamp which is optionally a part of a loading tray assembly such as that shown in FIG. 7. In further embodiments, occlusion means may be integrated into the flexible container, or may be a reusable piece of equipment external to the container. In embodiments, occlusion means must be capable of creating a temporary impermeable or substantially impermeable seal between the non-breathable section and the breathable section of the evolving multi-part lyophilization container.

The use of a physical barrier (e.g., a peelable seal) to segregate fluid in the non-breathable section from the breathable section according to workflows described above eliminates the potential for fluid contact with, and fouling of, the pores of breathable material in the breathable section. Membrane fouling can disrupt the sublimation and desorption aspects of lyophilization, thereby increasing total lyophilization time and reducing the ability to obtain a viable lyophilizate. Accordingly, eliminating the potential for fouling leads to a relative increase in vapor flow which, in turn, results in faster freeze drying, a colder ice temperature during primary drying due to an increased sublimative cooling effect and increased retention of proteins and clotting factors.

Moreover, because the lyophilization container is a closed, sterile system including sterile fluid pathways, embodiments enable lyophilization to occur in both non-sterile environments and in remote locations. In this respect, for example, embodiments allow lyophilization to be performed on-site at an ordinary blood center as opposed to a traditional clean room facility. Container embodiments also allow flexibility for an operator to freeze and maintain a frozen inventory of plasma in a standard freezer, such as that found in typical blood bank settings. At a later time, this previously frozen plasma can be moved to the more specialized lyophilization instrument for sublimation and desorption. Such work flow flexibility results in improved blood logistics and work flow within the blood bank.

A further advantage of embodiments described herein is the ability to remove the non-breathable section of the lyophilization container post-lyophilization. Isolation and removal of the breathable section post-lyophilization results in the creation of a smaller, lighter aseptic container enclosing the final lyophilizate. The resultant container is also both flexible and highly portable. Moreover, since the breathable section is most vulnerable to moisture and oxygen ingress, its removal can be said to improve the shelf stability of the lyophilizate. The novel use of a temporary occlusion described herein makes this advantage possible. That is, in conventional systems utilizing glass containers, a stopper is mechanically applied to a glass lyophilization container prior to the opening of the lyophilizer in order to prevent an ingress of moisture and oxygen into the container. In contrast, present embodiments utilize the temporary occlusion to prevent an ingress of moisture and oxygen into the non-breathable portion of the container until a permanent seal can be made between non-breathable material portions of the front and back of the container.

The ability of embodiments herein to evolve container configuration, yet to remain a closed, sterile system throughout each phase of container lifecycle is highly unique and advantageous in the lyophilization space. That is, the present embodiments evolve to achieve significant advantages over conventional devices and methods during each of filling, lyophilization, transportation, storage, reconstitution and infusion. Accordingly, many of the attributes and advantages described herein are not possible using conventional devices and approaches, which do not evolve and which require a clean room environment. Importantly in this regard, the evolving, multi-part containers described herein should be further considered evolving, multi-function containers insofar as the type and arrangement of container elements allow the container to accomplish various functions throughout its lifecycle.

Notwithstanding the various specific embodiments enumerated in this disclosure, those skilled in the art will appreciate that a variety of modifications and optimizations could be implemented for particular applications. Additionally, the present application is not limited to the lyophilization of blood or blood products. That is, the principles of the present application may be applicable to the lyophilization of many fluids. Accordingly, various modifications and changes may be made in the arrangement, operation, and details of the methods and systems of the present application which will be apparent to those skilled in the art.

What is claimed is:

1. A multi-part lyophilization container, the container comprising:
   a front surface;
   a back surface;
   a non-breathable section including a port region;
   a breathable section including a breathable membrane; and
   a peelable region including a peelable seal, the peelable region encompassing a boundary bridging the non-breathable section and the breathable section,
   wherein the peelable seal is configured to open in response to a pressure differential created between an inside and an outside of the non-breathable section of the multi-part lyophilization container.

2. The multi-part lyophilization container of claim 1, wherein the front surface and the back surface each comprise a portion of the breathable section including a breathable membrane.

3. The multi-part lyophilization container of claim 1, wherein the peelable region comprises dissimilar materials.

4. The multi-part lyophilization container of claim 1, wherein the peelable region comprises materials having dissimilar textures.

5. The multi-part lyophilization container of claim 1, wherein at least one material of the peelable region comprises an additive.

6. The multi-part lyophilization container of claim 1, wherein the peelable region comprises a visual indicator.

7. The multi-part lyophilization container of claim 1, wherein the peelable region has a width of approximately 0.95 cm.

8. The multi-part lyophilization container of claim 1, further comprising a Hold Open Device (HOD).

9. A method of lyophilizing a fluid in a multi-part container including a peelable seal, the method comprising:
   inputting the fluid into a non-breathable section of the multi-part container;
   freezing the fluid;
   applying, in a lyophilization chamber, vacuum pressure;
   opening the peelable seal using a pressure differential created between an inside and an outside of the non-breathable section of the multi-part container;
   applying heat energy;
   sublimating the fluid; and
   creating a temporary occlusion in a peelable region of the multi-part container.

10. The method of claim 9, further comprising inputting a gas into the non-breathable section of the multi-part container to create a vapor space above the inputted fluid.

11. The method of claim 9, further comprising backfilling the lyophilization chamber to a partial atmospheric pressure.

12. The method of claim 9, further comprising creating a permanent seal dividing a breathable section from the non-breathable section of the multi-part container.

13. The method of claim 12, further comprising removing the breathable section of the multi-part container.

14. The method of claim 13, further comprising removing a tear away tail from the breathable section of the multi-part container.

15. The method of claim 14, further comprising attaching the tear away tail to the non-breathable section of the multi-part container.

16. The method of claim 9, wherein the fluid is selected from among blood plasma, a cell suspension, a fluid containing cryoprecipitate and a fluid containing platelet lysate.

17. The method of claim 9, wherein the multi-part container further includes a Hold Open Device (HOD).

18. A method of manufacturing a peelable seal in a multipart lyophilization container, the method comprising applying heating elements of a heat-sealing machine to opposing materials of the multi-part lyophilization container at a continuous temperature of approximately 64° C. for approximately 40 seconds.

19. The method of claim 18, further comprising applying the heating elements to the opposing materials of the multi-part lyophilization container using a clamping force of approximately 50 Psi.

20. The method of claim 18, wherein the opposing materials are dissimilar.

21. The method of claim 18, wherein the opposing materials comprise dissimilar textures.

22. The method of claim 18, wherein the peelable seal has a width of approximately 0.95 cm.

* * * * *